United States Patent
Shapira

(10) Patent No.: US 7,241,933 B2
(45) Date of Patent: Jul. 10, 2007

(54) SYSTEM AND METHOD FOR ASSESSING FLUID DISTRIBUTION

(75) Inventor: Shmuel Shapira, Sherwood, OR (US)

(73) Assignee: Sysmore, Inc., Sherwood, OR (US)

( * ) Notice: Subject to any disclaimer, the term of this patent is extended or adjusted under 35 U.S.C. 154(b) by 491 days.

(21) Appl. No.: 10/666,021

(22) Filed: Sep. 17, 2003

(65) Prior Publication Data

US 2004/0078014 A1   Apr. 22, 2004

Related U.S. Application Data

(63) Continuation-in-part of application No. 10/253,807, filed on Sep. 23, 2002, now Pat. No. 6,916,968.

(60) Provisional application No. 60/494,031, filed on Aug. 8, 2003, provisional application No. 60/473,790, filed on May 27, 2003, provisional application No. 60/473,001, filed on May 22, 2003, provisional application No. 60/467,272, filed on May 2, 2003, provisional application No. 60/454,390, filed on Mar. 12, 2003, provisional application No. 60/452,703, filed on Mar. 6, 2003, provisional application No. 60/429,154, filed on Nov. 25, 2002, provisional application No. 60/373,637, filed on Apr. 19, 2002, provisional application No. 60/357,624, filed on Feb. 20, 2002, provisional application No. 60/354,530, filed on Feb. 8, 2002, provisional application No. 60/348,381, filed on Jan. 16, 2002, provisional application No. 60/344,795, filed on Jan. 7, 2002, provisional application No. 60/324,278, filed on Sep. 25, 2001.

(51) Int. Cl.
*A61F 13/15* (2006.01)
*G08B 23/00* (2006.01)
*G08B 17/06* (2006.01)
*G08B 21/00* (2006.01)

(52) U.S. Cl. ............. 604/361; 604/362; 340/573.6; 340/596; 340/604

(58) Field of Classification Search ........ 604/361; 340/618, 572.1, 573.6, 596, 604; 73/73; 338/34–38
See application file for complete search history.

(56) References Cited

U.S. PATENT DOCUMENTS

| 4,800,370 A | 1/1989 | Vetecnik |
| 5,570,082 A | 10/1996 | Mahgerefteh et al. |
| 5,959,535 A | 9/1999 | Remsburg |
| 6,091,336 A | 7/2000 | Zand et al. |

(Continued)

FOREIGN PATENT DOCUMENTS

JP   2001338827 A   7/2001

(Continued)

*Primary Examiner*—Jacqueline F. Stephens
(74) *Attorney, Agent, or Firm*—Kolisch Hartwell, P.C.

(57) ABSTRACT

A system and method for assessing fluid distribution. According to one aspect of the disclosure, a fluid detection network is used to assess the fluid distribution of a fluid collection article having a plurality of tested regions. Each tested region of the fluid collection article is serviced by the fluid detection network. The fluid detection network is configured to indicate a fluid distribution of the fluid collection article. According to another aspect of the disclosure, a monitoring subsystem assesses a fluid distribution of a test area serviced by a fluid detection network, wherein the fluid detection network has a net characteristic indicative of the fluid distribution of the test area.

27 Claims, 16 Drawing Sheets

U.S. PATENT DOCUMENTS

| | | |
|---|---|---|
| 6,359,190 B1 | 3/2002 | Ter-Ovanesyan et al. |
| 6,832,507 B1 * | 12/2004 | van de Berg et al. .......... 73/73 |
| 2002/0070864 A1 | 6/2002 | Jeutter et al. |
| 2002/0070868 A1 | 6/2002 | Jeutter et al. |

FOREIGN PATENT DOCUMENTS

| | | |
|---|---|---|
| JP | 2001289775 A | 10/2001 |
| JP | 2001325865 A | 11/2001 |

* cited by examiner

SYSTEM AND METHOD FOR ASSESSING FLUID DISTRIBUTION

CROSS REFERENCE TO RELATED APPLICATIONS

This application is a continuation-in-part of U.S. patent application Ser. No. 10/253,807, filed Sep. 23, 2002 now U.S. Pat. No. 6,916,968, which claims the benefit of U.S. Provisional Patent Application Nos. 60/324,278, filed Sep. 25, 2001; 60/344,795, filed Jan. 7, 2002; 60/348,381, filed Jan. 16, 2002; 60/354,530, filed Feb. 8, 2002; 60/357,624, filed Feb. 20, 2002; and 60/373,637, filed Apr. 19, 2002. This application also claims the benefit of U.S. Provisional Patent Application Nos. 60/429,154, filed Nov. 25, 2002; 60/452,703 filed Mar. 6, 2003; 60/454,390, filed Mar. 12, 2003; 60/467,272, filed May 2, 2003; 60/473,001, filed May 22, 2003; 60/473,790, filed May 27, 2003; and 60/494,031 filed Aug. 8, 2003. The content of the above referenced applications is herein incorporated by reference for all purposes.

BACKGROUND

In the past, detecting the presence of urine, for instance in a diaper or bedding, has been accomplished by physically touching the potentially wetted area. For convenience, speed, sanitation, and similar reasons, this method is less than ideal, particularly in a managed care environment. In such environments, urine detection is an ongoing process. Several patients may need to be repeatedly tested, which can be a time consuming, physically demanding, undesirable task. Often times, patients are in beds, covered with blankets, and testing for urine in such circumstances is difficult using conventional methods. Some detection methods utilize visual indicators, but these methods require removal of clothing and/or blankets, and cannot be discretely used by an adult wearing a diaper in public.

To maximize the utility of urine collection articles, such as diapers, such articles must be changed when they have collected the proper amount of urine. A person suffering from lack of bladder control may continuously leak urine, and the mere presence of urine in the article does not always necessitate a change. Changing a urine collection garment too soon can be wasteful because the maximum effectiveness of the garment is not utilized. Changing a garment too late may cause the wearer discomfort and/or irritation, and may also allow urine to spread outside of the garment. Therefore, to maximize the effectiveness of such garments, it is desirable to be able to determine the relative amount of urine that has been collected by such a garment so that the garment may be changed at the proper time. Industry experts estimate that absorbent articles are used to only about 30% of their capacity, which results in unnecessary expenditure by consumers and undesirable environment impact.

The distribution of urine within an absorbent article may be at least partially dependent on the pattern of use. With a diaper, for example, the body position of the person using the article (i.e. lying on back, lying on front, lying on left side, lying on right side, etc.) will influence the fluid distribution within the diaper. Gravity may cause retained fluid to collect at a portion of the article that is relatively low compared to other portions of the absorbent article. Because more fluid may be retained at the low side of the article, maximum capacity may be reached at that area or a leak may occur there before other areas of the article retain any fluid.

SUMMARY

A system and method for assessing fluid distribution is provided. According to one aspect of the disclosure, a fluid detection network is used to assess the fluid distribution of a fluid collection article having a plurality of tested regions. Each tested region of the fluid collection article is serviced by the fluid detection network. The fluid detection network is configured to indicate a fluid distribution of the fluid collection article. According to another aspect of the disclosure, a monitoring subsystem assesses a fluid distribution of a test area serviced by a fluid detection network, wherein the fluid detection network has a net characteristic indicative of the fluid distribution of the test area.

DETAILED DESCRIPTION

Figure 1:
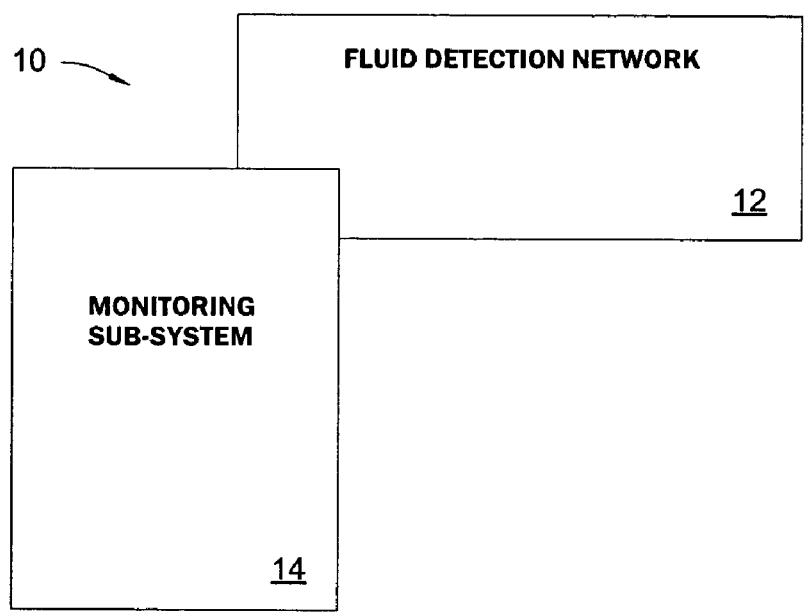
FIG. 1 is a schematic view of a fluid detection system.

FIG. 1 schematically shows a fluid detection system 10 that is configured to assess the distribution of a fluid. As used herein, the term "distribution" is used to describe the absolute and/or relative presence, quantity, and/or location of such a fluid. Fluid detection system 10 includes a fluid detection network 12 and a monitoring subsystem 14 that can be individually and collectively configured to detect a fluid distribution. The fluid detection network can be associated with different regions that are to be tested so that different portions of the fluid detection network correspond to different regions of the tested area. In other words, different portions of a fluid detection network may service different regions of a tested area. Each region may be monitored, thus allowing the fluid distribution throughout the tested area to be determined. A monitoring subsystem can cooperate with the fluid detection network to interpret information from the fluid detection network, and such information can be used to assess fluid distribution of the tested area.

Although the below disclosure describes exemplary systems that are configured to detect the distribution of urine in absorbent articles, it should be understood that this disclosure is not so limited. Such embodiments are provided for the purpose of teaching individual features, functions, elements, and/or properties that may be variously combined while remaining within the scope of this disclosure. Detecting urine in an absorbent article is provided as only one example of the broader application of detecting a fluid in a tested area.

Urine Detection Network

Figure 2:
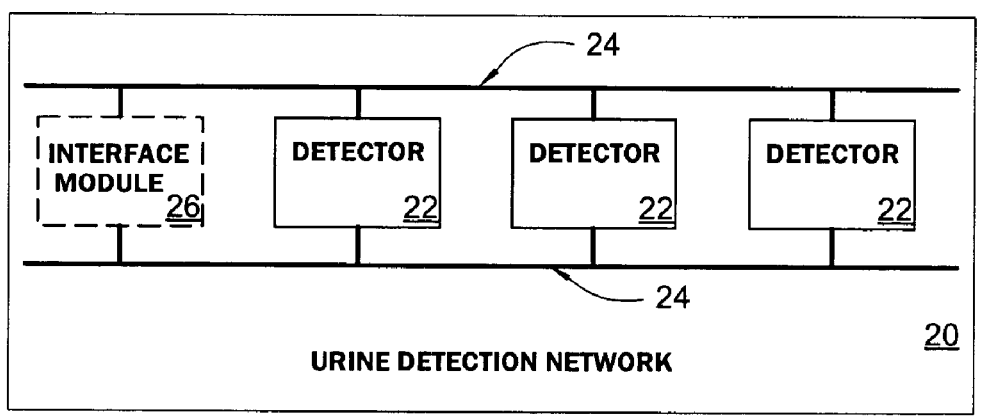
FIG. 2 is a schematic view of a urine detection network.

FIG. 2 schematically shows an exemplary fluid detection network 12 in the form of a urine detection network 20. Urine detection network 20 can be used to detect the distribution of urine in an absorbent article. As used herein, "absorbent article" is used to describe any article that can hold or contain variable amounts of fluid. Although described below in the context of a diaper, it should be understood that absorbent articles may also take the form of bedding, garments, sanitary napkins, etc. Furthermore, absorbent articles may be configured for collecting substances other than fluids and fluids other than urine. In general, it is within the scope of this disclosure to test the fluid distribution of virtually any absorbent medium or other item that may collect a fluid. A diaper is described as a single nonlimiting example of an absorbent article that may be tested.

Absorbent articles may include one or more regions, which may be tested in order to assess the degree to which each region has been wetted. For example, a diaper may include a front portion and a rear portion, which may respectively be wetted with different amounts of urine depending on whether a user is lying in a face-up or a face-down orientation. Accordingly, urine detection network 20 may include one or more detectors 22, which can be individually configured and positioned to test the relative or absolute urine content of such regions. In this manner, a network of detectors can collectively test different regions of an absorbent article to assess the location of urine throughout the absorbent article as opposed to the mere presence of urine without knowledge of its distribution. Different regions may be tested independently of one another, as groups of regions, or collectively as a whole. Furthermore, a network of detectors may indicate the remaining functional absorbent capacity of the article in one or more body positions, which in turn may be used to determine if a change can be postponed.

The tested regions may correspond to different usage patterns, and tested wetness levels of one or more regions may be used to determine the ability of an absorbent article to collect additional fluid without leaking. In some embodiments, the level of fluid in a region containing the most fluid relative to other regions may be interpreted as the fluid level of the article as a whole, although other regions may be less wetted or even unwetted. In some embodiments, the level of fluid in one region may be considered with respect to the wetness of other regions to determine if the absorbent article is capable of retaining additional fluid to adequately comply with its functional purpose. A network of detectors may be configured to provide information regarding the fluid distribution of the absorbent article, i.e. the relative or absolute wetness of one or more regions of the article. Such information may be used to assess the fluid distribution of the article. Accordingly, the fluid distribution may be used to make decisions corresponding to the absorbent article, such as whether a diaper needs changing.

A detector 22 may participate as an identifiable element within urine detection network 20. In some embodiments, two or more detectors may be interconnected via a bus 24. Bus 24 may include one or more series and/or parallel connections that operatively couple one detector to another. In some embodiments, a detector may be inductively or capacitively coupled to a bus. Furthermore, other network elements may be operatively coupled to bus 24. For example, FIG. 2 shows an interface module 26 coupled to bus 24. Bus 24 may be configured to effectively link two or more network elements, such as detectors 22 and/or interface module 26. In this manner, the individual functionality of a single network element may contribute to the collective functionality of the network as a whole, as is described in more detail below.

A detector 22 may be configured to test a region of an absorbent article using a variety of mechanisms. Detector 22 may be any element capable of translating the presence of urine, or another fluid or ionized substance, into a detectable change in a characteristic of urine detection network 20. As one example, a detector may change the net capacitance of a network when the region that the detector tests experiences a change in urine distribution. Such a change to the net capacitance of the urine detection network may be attributed to a change in the individual capacitance of the detector resulting from the presence of urine. Capacitance is provided as a nonlimiting example of a network characteristic that may be responsive to changes in urine distribution.

A network may include a detector with characteristics that distinguish it from other detectors of the network, so that a particular detector may be distinguished from other detectors. For example, at least one detector may be configured with known minimum and maximum capacitance values, which may be different from the minimum and/or maximum values of other detectors. Thus, a particular detector may change capacitance in a manner different from other detectors, and change the net capacitance of all detectors differently than any other detector, or combination of detectors. Therefore, if the capacitance of such a detector changes, because a region associated with it becomes at least partially wetted, the change in capacitance may be attributed to a wetting of the region serviced by that detector. Each detector may be configured with a unique capacitance, and the collective capacitance of all detectors, or any group of detectors, may be configured to signal different wetness conditions, which depend on the region or regions of the article that have been wetted.

In some embodiments, one or more detectors may be configured to have a known capacitance range, while other detectors do not have precisely identifiable capacitance ranges, but rather a range from a set value, or range, to a value out of a known range. Such an arrangement may be useful to determine whether a particular region of an absorbent article is sufficiently wetted so as to warrant a change. For example, this could be used to determine whether a diaper needs to be changed, without precisely identifying what region of the diaper is wetted; or whether a diaper change may be avoided although an identified region is detected as being wet.

A region serviced by an identifiable detector may be wetted, but because of the particular region associated with that detector, such as a region that is not prone to leaking, the diaper need not be changed if other detectors are not triggered. Nonetheless, the detector may be used to determine the overall remaining capacity of the collection article. Other regions, which when wetted indicate that a diaper should be changed, may be serviced by less predictable detectors that are not easily individually identifiable, because it has been predetermined that a diaper should be changed when any region associated with such a detector becomes wetted. In such circumstances, the precise region that has been wetted may not be indicated. The unpredicted capacitance may signal that a change is needed because the detectors that yield unpredicted capacitance values are positioned to service regions that correspond with a need to change the diaper when at least one of those regions is wetted. As used herein, the term "unpredictable" is used to describe a capacitance value outside of a predetermined range. It should be understood that an "unpredictable" value is useful in identifying wetness, because the capacitance has moved outside of a predetermined range. In some embodiments, the individual capacitance values of each detector, or groups of detectors, may be tested separately from other detectors, and in some embodiments the net capacitance of all detectors is tested.

A detector 22, or a portion of the detector, may be insulated from direct contact and/or galvanic interaction with urine. In other words, the detector can be configured so that portions of the detector, such as metal portions, do not physically interact with urine. The detector may be configured so that only materials that are relatively inert with respect to urine come into contact with urine. For example, an insulating layer, such as plastic, selected for its lack of reactivity with urine, may be used to shield a metal portion of a detector, which may undesirably react with the urine. Such a covering can prevent urine, which may be in contact with a user, from reacting with metal in a way that could be harmful to the user. However, insulating layers can be utilized without preventing the detector from performing its desired function of detecting urine.

A detector may be tuned to respond to the presence of urine if the urine exceeds a predetermined threshold amount and/or consistency. In some embodiments, such a threshold may be set to a nominal value so that any urine will exceed the threshold. In some embodiments, the threshold may be set to a more significant value so that an amount and/or consistency of urine below the selected threshold will not affect the urine detection network in the same manner as an amount and/or consistency of urine above the selected threshold. This may be useful in avoiding false positive detections resulting from small amounts of moisture in the vicinity of a detector. In some embodiments, a detector may respond to the relative amount of urine in the region serviced by the detector, and thus the detector may be used to determine the relative amount of urine in that region. In some embodiments, more than one detector may be associated with a region, and each detector in a region may be responsive to a different threshold of fluid.

A detector may be treated with a sensitizer to increase responsiveness to a targeted fluid. For example, a detector 22 may be treated with a fluid-soluble coating configured to dissolve, or otherwise change form, when a certain degree of saturation occurs. In some embodiments, an ionized substance, in a dried or other form, may be applied to the detector. In this manner, a fluid, including an unionized fluid, and the ionized substance may combine to form an ionized solution, which may increase detector sensitivity to some fluids and/or enable detection of fluids that would not otherwise be detectable. In some embodiments, the detectors may include a fluid collecting pad or sponge designed to retain fluid. Such pads may be treated with an ionized solution and dried, thus leaving an ionized substance on the pad. The ionized substance may react with ionized and/or unionized fluids to facilitate detection of the fluids.

A detector may include a dielectric portion configured to change dielectric properties in response to the presence of fluid. For example, in some embodiments, a detector may include opposing plates separated by a variable dielectric, such as a pad or a sponge, that changes the capacitance of the detector in response to changes in the wetness level of the pad. The wetness level of the pad may vary according to the degree of wetness around the pad. The change of capacitance in a single detector can produce a corresponding change in the net capacitance of a network. As described above, one or more detectors may be configured to change the net capacitance by a different amount than one or more other detectors. The network may be tested to determine a wetness condition corresponding to the region the detector services. For example, in embodiments where capacitance is a network characteristic that changes in response to wetness, the net capacitance of the network may be measured or otherwise analyzed to test the network.

In some embodiments, a detector may be configured so that the distance between portions of the detector mechanically changes when fluid is introduced to the detector. For example, a dielectric portion may expand and/or shrink with changing levels of wetness, thus changing the distance between opposing plates. In some embodiments, a dielectric layer may dissolve when exposed to a targeted fluid. In some embodiments, the dielectric layer may change dielectric properties in another manner. In any case, such changes can be measured and/or analyzed to assess saturation corresponding to a detector. The above are provided as nonlimiting examples, and other detection mechanisms may additionally or alternatively be implemented.

Figure 3:
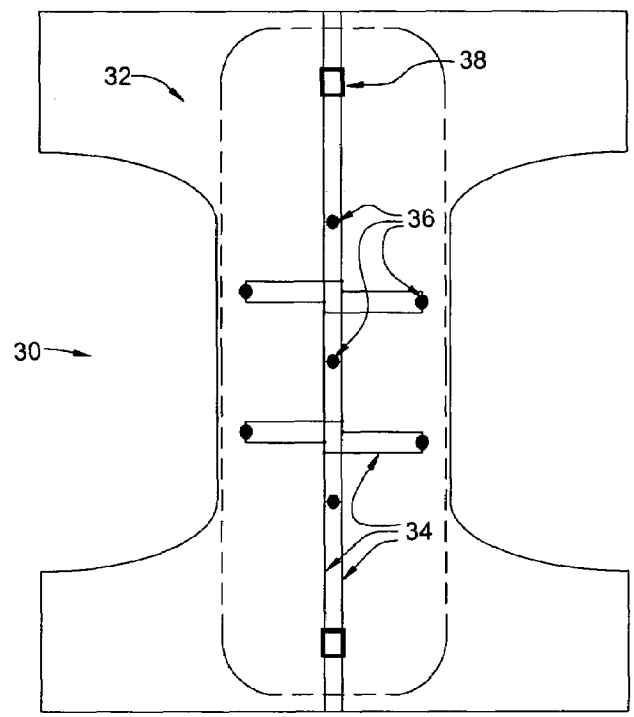
FIG. 3 is a schematic view of a diaper serviced by a urine detection network.

FIG. 3 schematically shows a diaper 30 that includes a urine detection network 32. The urine detection network includes a bus 34 that interconnects detectors 36. As can be seen, the detectors are located proximate different regions of diaper 30. Each detector is configured to test the region corresponding to that detector's position. Urine detection network 32 also includes an interface module 38 that facilitates communication with an external device. The incorporation of urine detection network 32 into diaper 30 is provided as a nonlimiting example of a fluid detection network servicing an absorbent article. It should be understood that other arrangements are contemplated. Furthermore, one skilled in the art of fluid detection may apply the above concepts to other fluid detection systems that service other types of tested areas. A urine detection network, or portions thereof, may be positioned inside an outer protective layer of the diaper, or outside of the outer protective layer.

Figure 4:
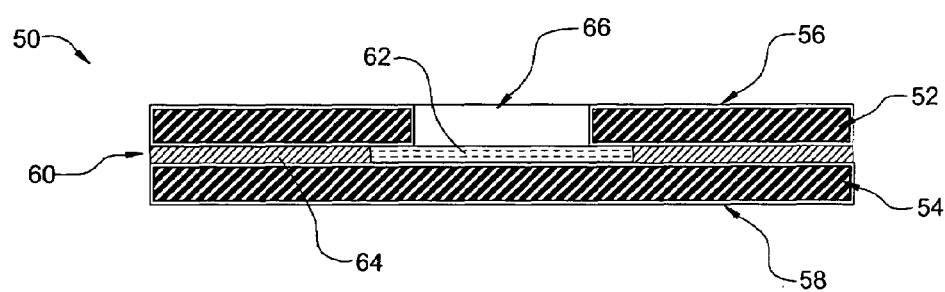
FIG. 4 is a schematic view of a detector as used in a fluid detection network.

FIG. 4 shows a schematic cross section of an exemplary detector 50. Detector 50 includes plate 52 and plate 54, which oppose one another. The plates may be constructed from metal sheet material, or another suitable conductor. The plates can be respectively sealed from moisture by insulating layer 56 and insulating layer 58. The insulating layers may be constructed from plastic or another waterproof coating material. The insulating layers may be configured to allow a plate to electrically communicate with a bus, which may or may not be insulated, while preventing undesired contact with a fluid. The insulating layers may be implemented in virtually any form that effectively seals selected portions of the plate from undesired fluid contact. In some embodiments, a single segment of insulating layer may effectively encapsulate a plate, and in some embodiments two or more portions of insulating layer may cooperate to collectively seal a plate. It should be understood that a sealed plate may connect to a bus.

Between plate 52 and plate 54, detector 50 includes dielectric material 60. In the illustrated embodiment, dielectric material 60 includes moisture absorbing portion 62 and a nonabsorbing portion 64. The absorbing portion is exposed to fluid via an opening, shown generally at 66. Absorbing portion 62 is configured to change dielectric properties when exposed to fluid. Therefore the capacitance of detector 50 changes when the detector is exposed to fluid. The change in capacitance may be analyzed to assess the wetness condition of the region associated with the detector. The above is only one example of a detector that may be implemented to assess fluid distribution at a tested area. Other configurations designed to respond to changes in fluid concentration with changes in capacitance may additionally or alternatively be used, and configurations designed to vary a characteristic other than capacitance may be used in some embodiments.

Figure 5:
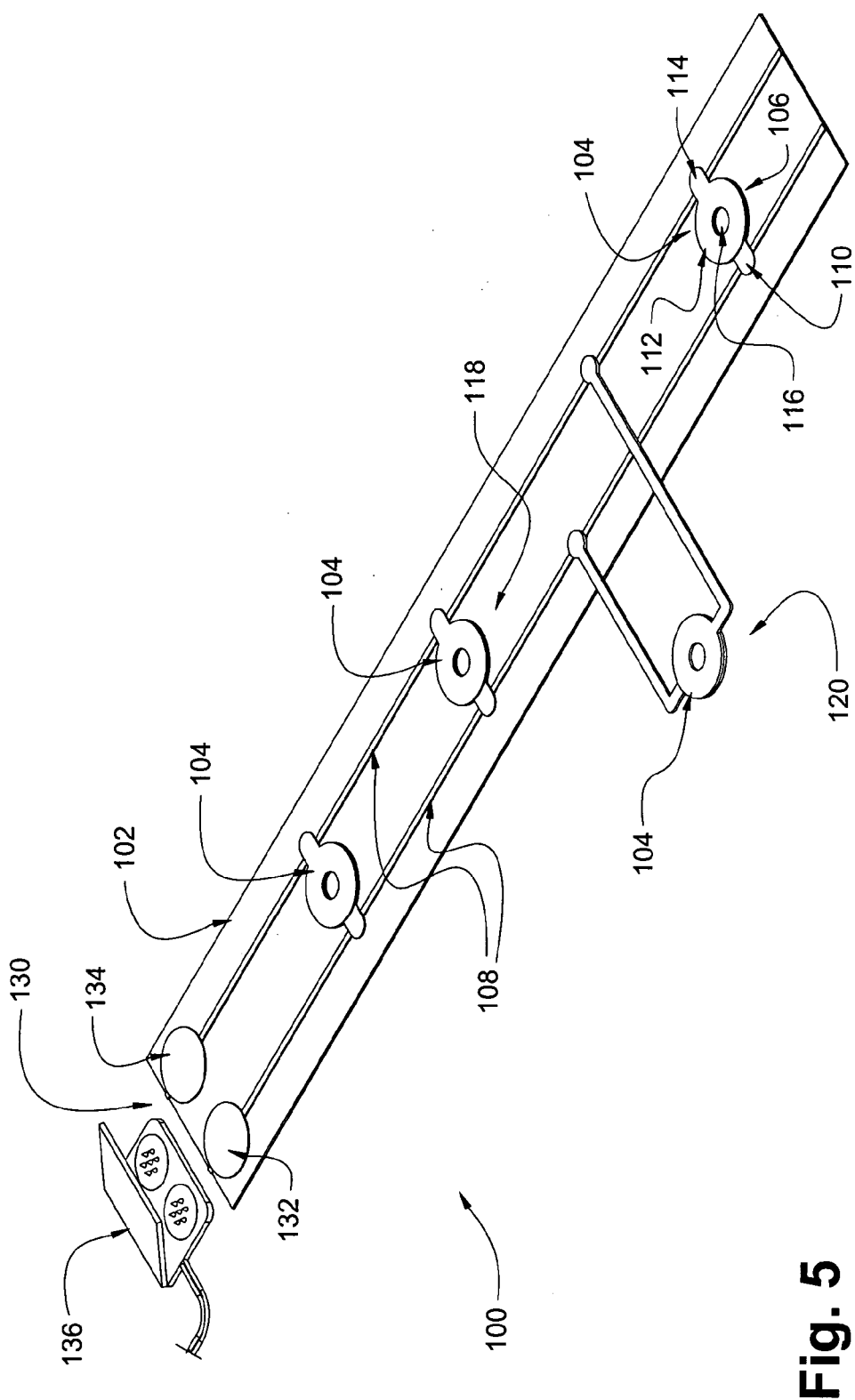
FIG. 5 is a somewhat schematic view of an embodiment of a urine detection network.
Figure 6:
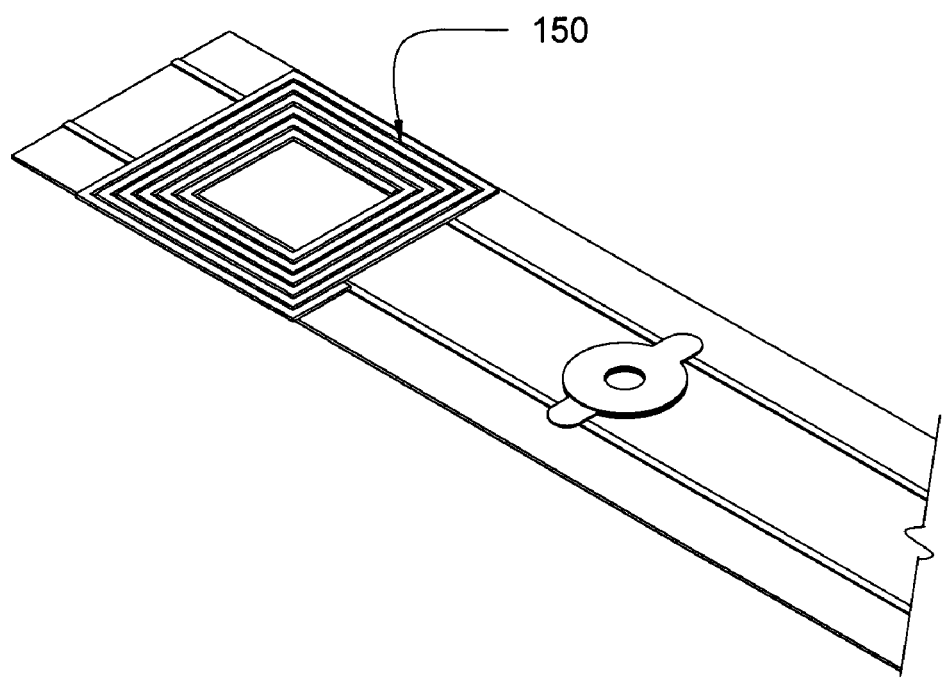
FIG. 6 is a somewhat schematic view of an embodiment of an interface module of a urine detection network.

FIG. 5 shows an exemplary urine detection network 100 configured as a sheet 102, which may be incorporated into an absorbent article. Constructing urine detection network 100 as a single sheet may simplify assembly of the absorbent article. For example, diapers may be assembled in layers by automated machines. A protective shell, absorbent core, inner fabric, and/or other portions may be layered together, cut, shaped, glued, etc. Furthermore, additional components such as elastic bands, fasteners, reinforcement supports, etc. may be used in the construction. Sheet 102 may be incorporated into such an assembly process, so that the sheet is layered with the other portions of the diaper. In some embodiments, a pick-and-place arrangement may be used to position a urine detection network, or portions thereof, at a desired location within the diaper during assembly. Such sheet arrangements may include a urine detection network assembled with a single wire, an assembly of capacitor plates, wires, and/or other components, or any other suitable urine detection network.

Urine detection network 100 includes detectors 104 that are configured to respond to the presence of urine by changing capacitance. A detector 104 may be constructed with the same general layout as detector 50 of FIG. 4, or other suitable arrangements may alternatively be used. Each detector 104 includes a first plate 106 electrically coupled to a bus 108 at a first node 110 and a second plate 112 electrically coupled to the bus at a second node 114. The plates may be effectively insulated from fluid using any suitable means, including covering the plates with an insulating layer. The plates may be positioned on opposing sides of a dielectric material, such as pad 116. As shown, at least a portion of the dielectric may be exposed so that urine may come into direct contact with the dielectric. The dielectric may be configured with an absorbent portion that changes dielectric properties when it absorbs fluid, and or other substances. Therefore, measurement of the capacitance of the fluid detection network may be used to assess the presence of fluid.

As shown, urine detection network 100 includes a network bus 108, to which detectors 104 are coupled. Some detectors may be connected immediately adjacent the network bus, as indicated at 118, while others may be spaced away from the bus, as indicated at 120. FIG. 5, shows only one possible arrangement, and it should be understood that detectors may be positioned to correspond to virtually any region of an absorbent article at which testing is desired. Furthermore, fluid detection networks may be configured to service tested areas other than absorbent articles and may be configured accordingly. One or more network busses may be used to facilitate placement of the various detectors that constitute a fluid detection network.

A fluid detection network may include an interface module configured to facilitate interaction with a monitoring subsystem. In this manner, information corresponding to a fluid distribution tested by the network may be acquired and/or interpreted by the monitoring subsystem. The monitoring subsystem may use an interface module that is complementarily configured relative to an interface module of the tested fluid detection network. Some monitoring subsystems may include interface modules that are configured to wirelessly acquire information from a fluid detection network, and/or to communicate via a direct electrical connection. Although primarily described herein with reference to wirelessly communicated electromagnetic energy and electrical energy communicated via direct electrical connection, it should be understood that fluid detection networks may be configured to operate and/or communicate using other energy forms, including optical energy and mechanical energy.

FIG. 5 shows an exemplary interface module in the form of a connection node 130. Connection node 130 includes electrical contact 132 and electrical contact 134, which are operatively coupled to a bus 108 of the urine connection network. Bus 108 may be connected to a detector 104 that is configured to respond to the presence of urine. One or more interface modules may be included in the same fluid detection network, thereby facilitating different types of interaction with a monitoring subsystem and/or providing different areas of the tested article with which the monitoring subsystem may establish interaction.

A monitoring subsystem may be clipped or otherwise coupled to connection node 130, thus allowing the monitoring subsystem to monitor a characteristic, such as capacitance, of the fluid detection network. In the illustrated embodiment, a clip 136 of a monitoring subsystem is shown in position to establish a charge path between connection node 130 and the monitoring subsystem. Other arrangements are possible, and the above is shown as a nonlimiting example. For example, in some embodiments, connection node 130 may be configured to extend out of a diaper where an electrical connection can be easily made. In general, a physical or operative connection may be established between conductors of a monitoring subsystem and a connection node of a fluid detection network, thus facilitating the transmission of electrical current between the monitoring subsystem and the fluid detection network. The type of the connection and the location of the connection may vary. The monitoring subsystem may be configured to measure characteristics of the fluid detection network, including the capacitance of the network. In some embodiments, electrical contact 132 and electrical contact 134 may facilitate capacitive coupling between the network and the monitoring subsystem.

Figure 20:
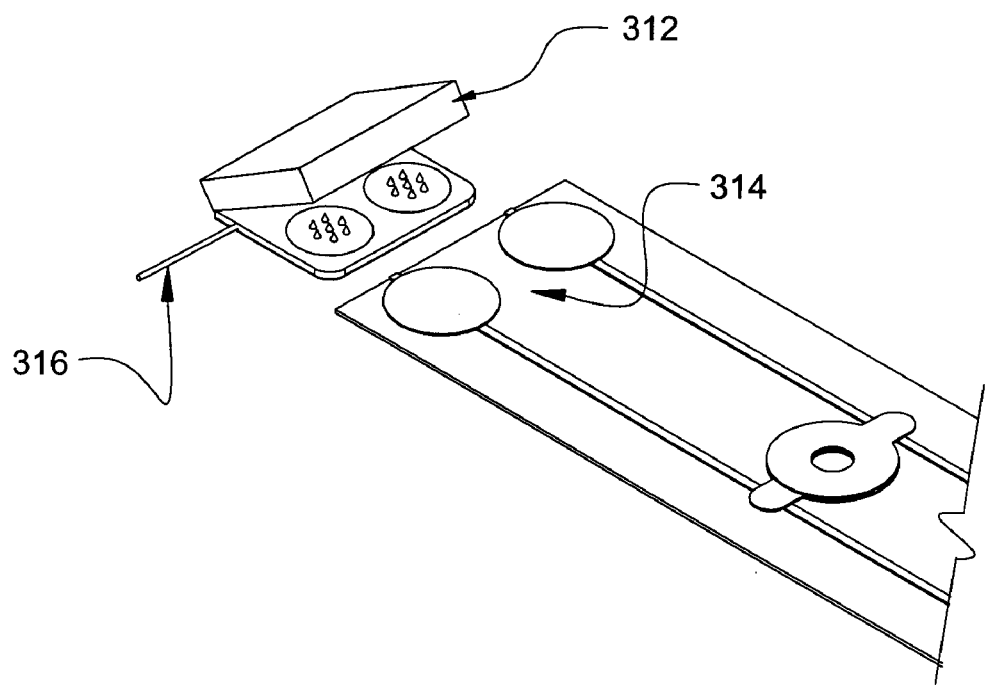
FIG. 20 is a somewhat schematic view of a signal generator configured to couple to a fluid detection network.

FIG. 20 shows an exemplary interface module in the form of an energy-converting module 150. Energy-converting module 150 may be coupled to a bus of a urine detection network. The energy-converting module may be configured to collaborate with a monitoring subsystem, thus wirelessly conveying information about the urine detection network to the monitoring subsystem. For example, a monitoring subsystem may generate a magnetic or electromagnetic field that energizes energy-converting module 150. As the urine detection network changes capacitance in response to changing fluid distributions, the changing capacitance may produce corresponding changes in the energy distribution between the monitoring subsystem and energy-converting module 150. Therefore, the monitoring subsystem may be used to monitor the capacitance of the fluid detection network, which predictably changes in response to the fluid distribution. In this manner, the energy distribution between the monitoring subsystem and energy-converting module 150 may be monitored to determine the fluid distribution.

Figure 7:
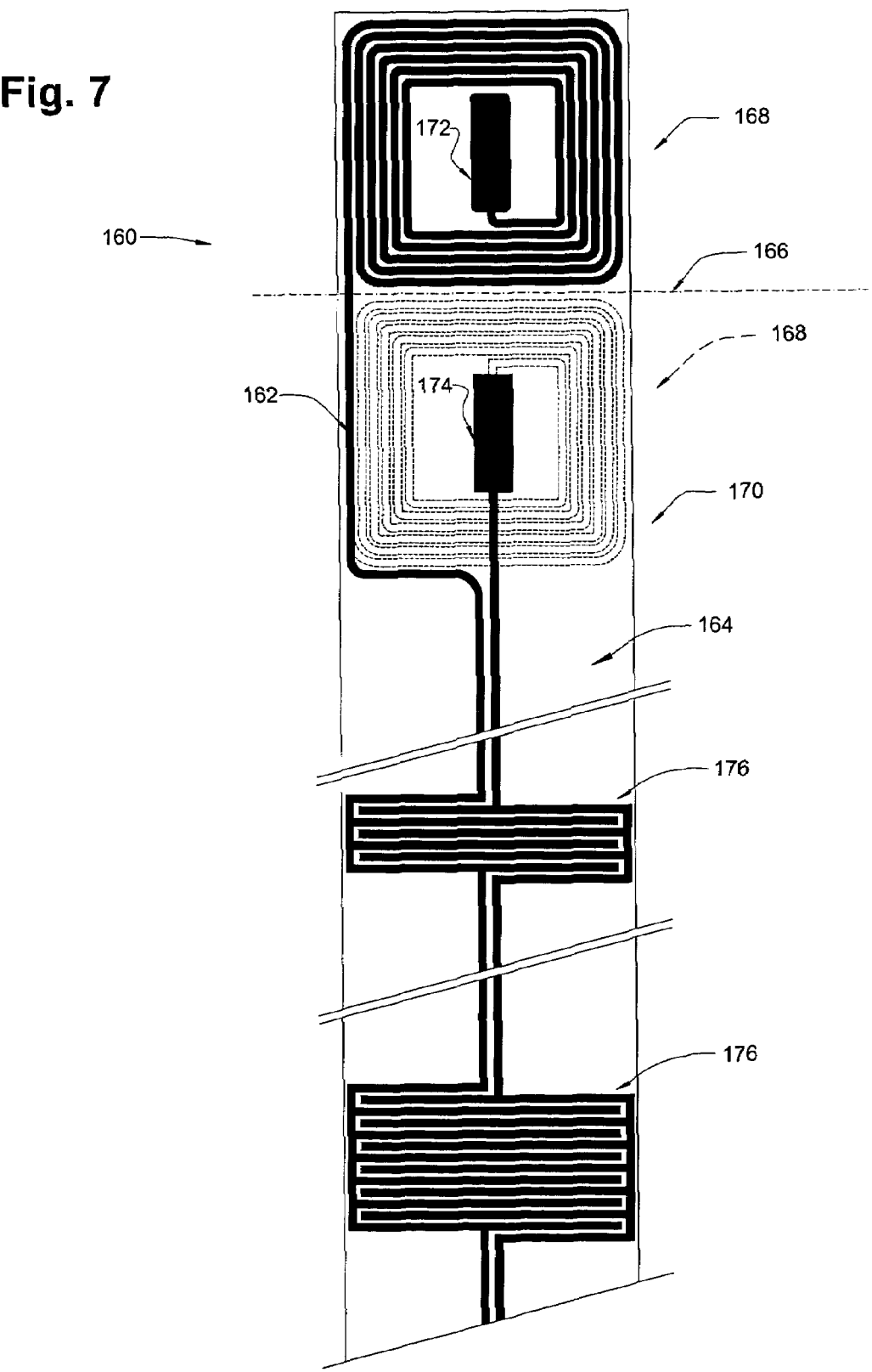
FIG. 7 is a schematic view of an embodiment of a urine detection network.

FIG. 7 shows a schematic view of an exemplary fluid detection network 160 that is made from a single layer of conductive material 162, such as aluminum foil, conductive ink, or the like. The conductive material is originally arranged in a generally planar configuration, and may be disposed on a dielectric material 164. When in an initial planar configuration, the conductive material is not in a final desired orientation. Folding along a fold line 166 so that a portion 168 of the conductive material is placed adjacent another portion 170 of the conductive material positions the conductive material in the desired configuration. In other words, folding the conductive material completes a desired circuit. A node 172 of portion 168 can be physically connected to a node 174 of portion 170 to form a charge path. In some embodiments, node 172 and node 174 may be capacitively coupled, or in other words, separated by a dielectric layer. Once folded, portion 168 and portion 170 collectively serve as an interface module, which may interact with a monitoring subsystem. Other network elements, such as detectors, may also be formed from folding a single layer into two or more adjacent layers.

Fluid detection network 160 includes detectors 176, which include insulated conducting plates that are positioned side by side in a planar configuration. In such an arrangement, ionized fluid may function similar to a second opposing plate, as found in a conventional capacitor. For example, ionized fluid covering the plates of detectors 176 may enable the plates to temporarily store charge and affect the fluid detection network's overall capacity. In other words, when ionized fluid covers a detector of the network, the detector's capacity may change accordingly. A layer of absorbent material may be positioned on top of a detector to ensure complete coverage by the fluid. Furthermore, a second layer of conductive material such as aluminum foil may be placed on top of the absorbent layer and may improve detection resolution between dry and wet detectors. The plates of the detectors may be insulated from fluid by a sheet of dielectric material and/or by applying an overcoat of dielectric material. Detectors may be configured with different sizes to enable distinguishing between the different detectors.

Figure 8:
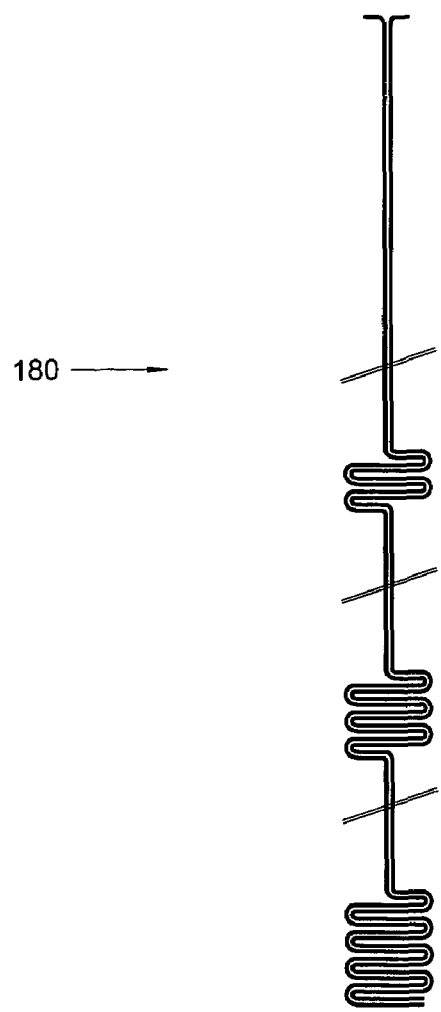
FIG. 8 is a schematic view of another embodiment of a urine detection network.

FIG. 8 depicts a schematic view of an exemplary fluid detection network 180 that is constructed from two parallel conductors separated by a dielectric layer. Portions of the dielectric layer, such as portions associated with detectors, may be designed to react in a predictable manner when fluid is present. For example, a dielectric property of that portion of the dielectric layer may change when exposed to a tested fluid. Other portions, such as portions not associated with a detector, may be kept from reacting to the fluid. To avoid reacting, such portions may be impregnated with a suitable compound, physically insulated, and/or otherwise protected.

Figure 9:
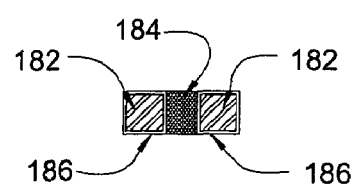
FIG. 9 is a schematic cross section view of an embodiment of a urine detection network.
Figure 10:
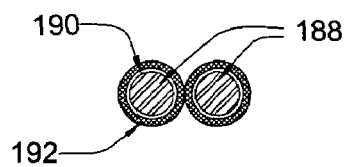
FIG. 10 is a schematic cross section view of another embodiment of a urine detection network.

The conductors and dielectric layer of fluid detection network 180 may be arranged in a variety of configurations. For example, FIG. 9 shows a cross section of one possible arrangement, in which parallel conductors 182 are arranged on opposite sides of a common absorbent dielectric layer 184. The conductors are surrounded by an insulation layer 186. FIG. 10 shows another arrangement, in which conductors 188 are covered by an insulation layer 190, which in turn is covered with a dielectric layer 192. In these or other embodiments, the dielectric layer may be absorbent and/or chemically reactive. The above are provided as nonlimiting examples. Other arrangements with absorbent or nonabsorbent dielectric layers may be used. In some embodiments, the dielectric layer may itself provide insulation, thus rendering a separate insulation layer unnecessary. As with other types of fluid detection networks, the overall capacity of a dry network can be established and changes that occur at any detector of the network may be detected and used in assessing fluid distribution.

Figure 11:
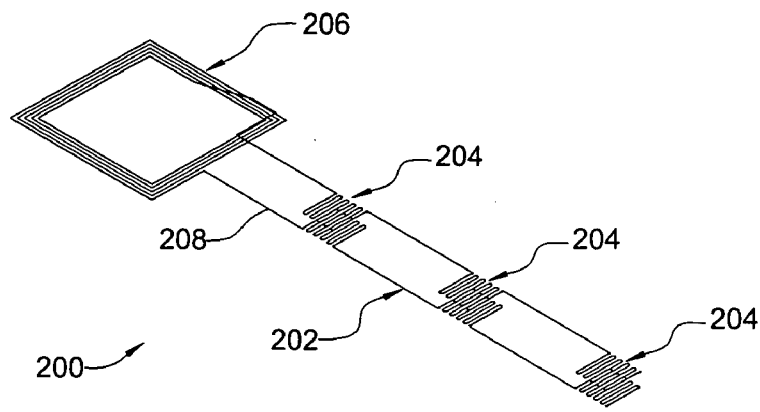
FIGS. 11–13 are schematic views of urine detection networks constructed from a single conductive element.
Figure 12:
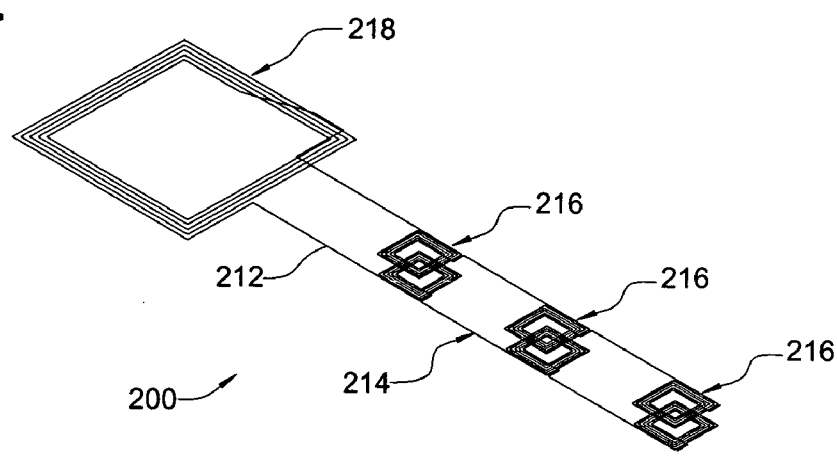
Figure 13:
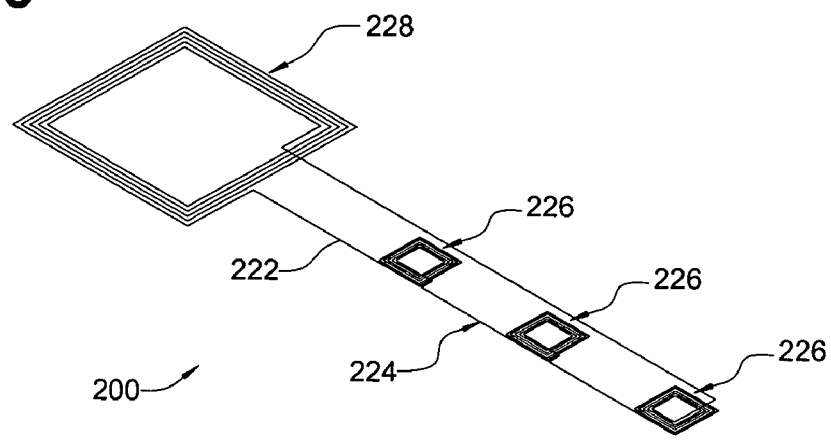

FIGS. 11–13 show three exemplary fluid detection network arrangements that include a single conductive element arranged to form one or more detectors, a bus, and/or additional elements. In some embodiments, the single conductive element may take the form of a moisture-insulated wire. Constructing the fluid detection network from a single conductive element may decrease the cost of the fluid detection network. The conductive element may be shaped to form detectors at a plurality of locations, which may be used to test the wetness at each location. While the bus, detectors, and/or interface module of a fluid detection network may be formed from a single conductive element, it should be understood that insulating layers, dielectric portions, and other components may also be used to construct such a fluid detection network.

FIG. 11 shows fluid detection network 200, which includes bus 202, detectors 204, and an interface module 206 fashioned from a single conductive element 208. Detectors 204 may function as simple capacitors. As described herein, capacitors may be configured to effectively measure the wetness of a tested area by changing capacitance in response to changes in wetness. To facilitate such measurements, materials that change dielectric properties in response to wetness may be utilized in some embodiments. Interface module 206 may be used to wirelessly interact with a monitoring subsystem, such as via mutual inductance. FIG. 12 shows a fluid detection network 210 in which a single conductive element 212 is shaped to form a bus 214, detectors 216, and an interface module 218. Detectors 216 are formed in a coil pattern. In response to wetness, a detector including a coil shaped element may change capacitance, and/or change its own inductive behavior, which may cause a measurable change in the overall energy absorption pattern of a fluid detection network. FIG. 13 shows yet another exemplary fluid detection network 220 in which a single conductive element 222 is shaped to form a bus 224, detectors 226, and an interface module 228. Detectors 226 are shaped as coils, and in some embodiments the detectors may be at least partially exposed to fluid while other elements of the network are insulated.

A variety of methods may be used to form a fluid detection network in which a single conductive element is shaped to form plural network elements, such as a bus, detectors, and/or interface module. For example, a wire may be bent into shape, conductive ink may be used to print a desired pattern, conductive sheet material may be cut or etched, etc. In general, methods which minimize cost while maximizing repeatability and speed of production are favored.

Figure 14:
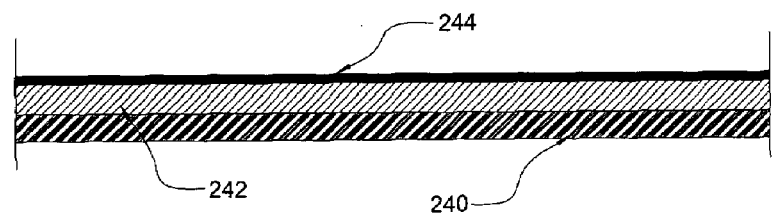
FIGS. 14–17 show a method of constructing portions of a fluid detection network from sheet material.

FIGS. 14–17 show an exemplary method of shaping a sheet of conductive material into a desired pattern, which may be used as part of a fluid detection network. FIG. 14 shows a cross section of a portion of sheet material that can be used to form a fluid detection network. The sheet material includes a substrate 240, a binder 242, and a conductive layer 244. The substrate may include plastic and/or another poor electrical conductor that is relatively chemically inert with respect to urine or another tested substance. In some embodiments, the substrate may be flexible, so as to increase placement options in urine collection articles such as diapers. Conductive layer 244 is generally formed from a conductive sheet material suitable for establishing one or more charge paths, through which electrical charge may move. In some embodiments, the conductive layer may include a metallic sheet material, such as an aluminum foil, or another flexible conductor. Binder 242 is intermediate substrate 240 and conductive layer 244. As explained below, in some embodiments, the binder may be a selectively deformable layer that can be given a desired profile. For example, binder 242 may include a hot melt adhesive capable of adhering conductive layer 244 to substrate 240. Such a hot melt adhesive may be stamped, embossed, or otherwise physically altered to have a desired shape. In some embodiments, a single layer may serve as the binder and the substrate. For example, a thermoplastic substrate/binder may serve as a substrate to a laminated conductive layer, the thermoplastic substrate/binder may be heated and shaped to help establish and maintain a suitable gap distance, as described below.

Figure 15:
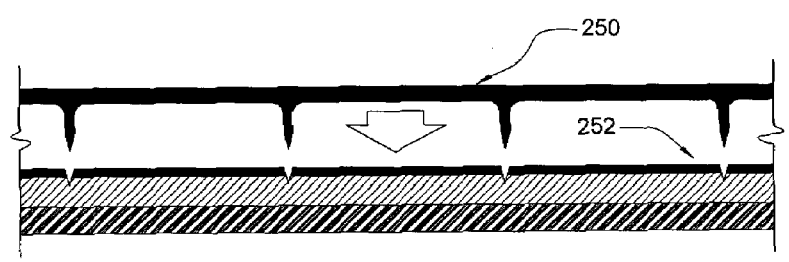

As shown in FIG. 15, a scorer 250 may be used to mark a pattern on conductive layer 244. In some embodiments, the scorer may take the form of a die cutting plate that is configured to physically cut through the conductive layer, and possibly a portion of the binder and/or the substrate. Cutting through the conductive layer effectively shapes the conductive layer into a desired conductive pattern 252. At least a portion of the binder and/or substrate may be left intact, thus providing a stable base for the newly formed conductive pattern. The conductive pattern may include adjacent traces, separated by a gap distance D. After the scorer disengages the conductive layer, Gap distance D may become very small or even closed.

Figure 16:
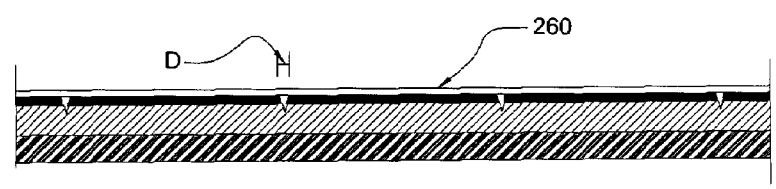

As shown in FIG. 16, a cover layer 260 may be applied on the conducting layer, or portions thereof. Cover layer 260 may be applied before or after shaping. Cover layer 260 may be contoured to the shape of the pressed conductive layer, or the cover layer may remain substantially flat. Cover layer 260 may include plastic, or another suitable material, which may effectively act as an electrical insulator. Cover layer 260 and substrate 240 may cooperate to seal the conductive layer, or at least selected portions of the conductive layer. Cover layer 260 may also facilitate maintaining a desired gap distance D between adjacent traces of the conductive layer.

Figure 17:
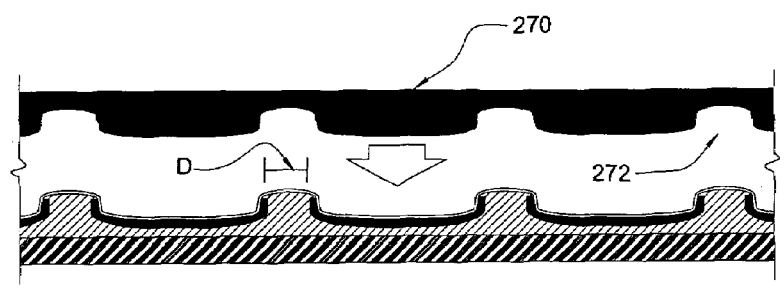

As shown in FIG. 17, a shaper 270 may be used to further define conductive pattern 252. In some embodiments, the shaper may take the form of a heated embossing plate. The shaper may be configured with a stamping pattern 272 that complements conductive pattern 252. The stamping pattern and the conductive pattern may be aligned, and the stamping pattern may be pressed into the conductive pattern. As shown, the conductive layer, binder, and/or cover layer may be deformed by the pressure of the shaper. In particular, the conductive layer may be given a more three-dimensional profile, which can increase a gap distance D between adjacent traces of the conductive layer. An increased gap distance may improve circuit integrity and help limit electrical shorts or other conditions that could cause a fluid detection network to behave unpredictably.

Figure 18:
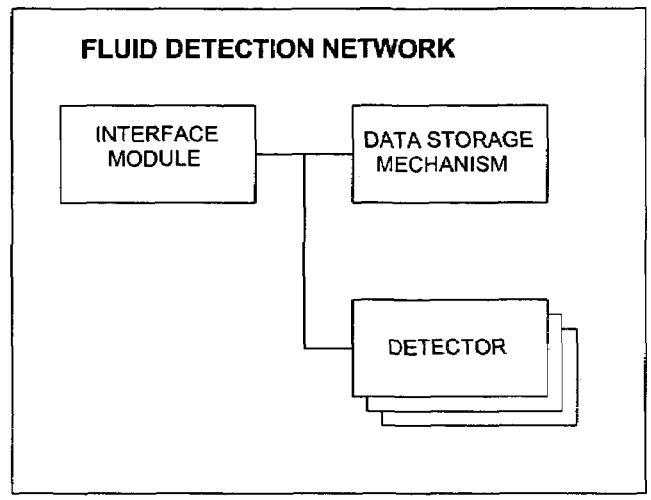
FIG. 18 is a schematic view of a urine detection network that includes a data storage mechanism.

As schematically shown in FIG. 18, a fluid detection network 280 may include a data storage mechanism 282 for storing information. For example, a fluid detection network may include a memory that stores an identifier that may be presented to a monitoring subsystem to facilitate identification of the particular fluid detection network. This may be useful, for example, if a common monitoring subsystem is used to test more than one fluid detection network. In particular, a data storage mechanism may include information regarding the type, size, and/or capacity of an absorbent article that the interface module is associated with, thereby allowing customized quantitative measurements to be performed.

To facilitate a wireless exchange of information between a monitoring subsystem and the fluid detection network, one or more energy-converting modules may be operatively coupled to the fluid detection network. An energy-converting module may facilitate the exchange of energy between the fluid detection network and a monitoring subsystem. The exchange of energy may be measured and/or analyzed by the monitoring subsystem. A characteristic of the fluid detection network may correspond to the energy exchange between the fluid detection network and the monitoring subsystem. In particular, one or more of the fluid detection network's characteristics, such as capacitance, may be determined based on the monitored energy exchange.

In some embodiments, an energy-converting module includes a coil coupled to a fluid detection network bus. The coil may be configured to convert energy generated by an inducer into electromotive force within the fluid detection network. An energy distribution between the fluid detection network and the inducer may be measurably influenced according to the capacitance, or other characteristic, of the fluid detection network. Therefore, measurement and analysis of the energy distribution pattern may be used to detect the distribution of urine.

Monitoring Subsystem

Figure 19:
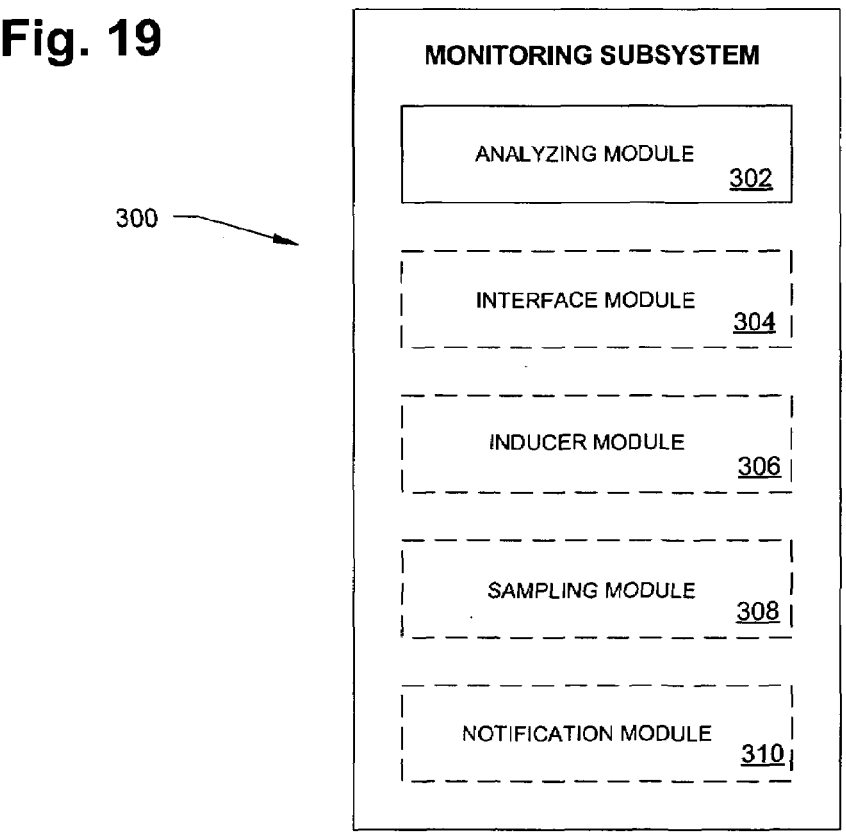
FIG. 19 is a schematic view of a monitoring subsystem.

FIG. 19 schematically shows an exemplary monitoring subsystem 300. A monitoring subsystem may take the form of a portable device, which may be moved from one testing location to another. In some embodiments, a monitoring subsystem may include a combination of stationary and portable componentry, which may be constructed as two or more separate devices. A monitoring subsystem may be configured for measuring and/or analyzing fluid distribution independent of other devices, or a monitoring subsystem may be configured to cooperate with one or more other devices to measure and/or analyze fluid distribution. A monitoring subsystem may be adapted to present information to other devices for analysis and/or notification via wired or wireless transmission modes. In some embodiments, the monitoring subsystem may send or receive data that may be interpreted or further analyzed to determine a fluid distribution. Furthermore, elements of the monitoring subsystem may transmit raw and/or analyzed data to other elements of the monitoring subsystem or to another device via wired or wireless communication. Such data may be further analyzed, recorded, validated, reported, etc. For the purpose of simplicity, this disclosure primarily focuses on a monitoring subsystem that is configured as a unitary portable device. However, monitoring subsystems constructed of two or more devices are also within the scope of this disclosure. Furthermore, while described in the context of measuring and analyzing a fluid distribution, it should be understood that detection networks may be configured for different types of measurements, and monitoring subsystems may be used to wirelessly assess information obtained from such measurements.

Monitoring subsystem 300 includes an analyzing module 302. As indicated in dashed lines, monitoring subsystem 300 may also include an interface module 304, an inducer module 306, a sampling module 308, and/or a notification module 310. Analyzing module 302 may be configured to analyze information in order to assess the fluid distribution of a tested area serviced by a fluid detection network. Analyzing module 302 may include hardware, firmware, and/or software used to perform measurements and/or analysis. As nonlimiting examples, an analyzing module may take the form of a circuit board designed for the specific purpose of analyzing a fluid detection network, or an analyzing module may take the form of a general computer capable of running software designed to analyze a fluid detection network. In a simple embodiment, the analyzing module may include componentry for directly measuring the capacitance of a fluid detection network. In some embodiments, the analyzing module may be configured to perform data analysis, as described in more detail below.

A monitoring subsystem and a fluid detection network may be communicatively coupled by an information link. The information link may be a wired or wireless connection. In some embodiments, the analyzing module may acquire information for analysis via an interface module 304 that is physically coupled to a connection node of a fluid detection network. In some embodiments, the analyzing module may wirelessly acquire information for analysis. Information may be wirelessly acquired via an inducer module 306 and/or a sampling module 308. In either case, acquired information may be delivered to the analyzing module via a direct connection, such as an electrical or optical connection, or the information may be wirelessly transmitted, such as via a radio signal.

When present, an interface module 304 may electrically couple to a connection node of a fluid detection network, thus electrically linking the connection node of the fluid detection network to analyzing module 302. In this manner, analyzing module 302 can read the net capacitance (or other characteristic) of the urine detection network via a direct physical connection. FIG. 5 shows an example of a connection node to which interface module 304 may connect. As mentioned above, connection nodes may be placed for easy access, so that fluid distribution measurements may be easily taken. Though schematically shown as a simple clip arrangement, it should be understood that a more robust interface may be utilized for coupling a fluid detection network to a monitoring subsystem.

In some embodiments, an interface module in the form of a wireless signal generator may be directly coupled to a fluid detection network. For example, as shown in FIG. 20, a self-powered signal generator 312 may be coupled to a bus of a urine detection network via a connection node 314. Signal generator 312 may be configured to produce a signal that may be received and/or analyzed by a monitoring subsystem. In the illustrated embodiment, signal generator 312 is directly coupled to the network and configured to predictably change aspects of the produced signal (frequency, modulation, duty cycle, etc.) in response to changes in the capacitance of the network. In other words, urine distribution around the corresponding urine detection network controls the capacitance of the urine detection network, and the capacitance of the urine detection network controls at least one aspect of a signal produced by signal generator 312. Analyzing module 302 may be configured to receive the broadcast signal and determine the capacitance of the network. In this manner, the urine distribution of a tested area can be assessed.

Signal generator 312 may include an internal or external antenna 316 configured to facilitate signal transmission. The signal generator may also include a battery, or other power source, used to power signal production, and/or the signal generator may utilize power delivered via transmitted electromagnetic energy to generate a signal for transmission. In some embodiments, other configurations of signal generators may be employed for transmitting raw and/or analyzed data.

In some embodiments, a direct reading of capacitance, or another network characteristic, is not taken. Instead, a fluid detection network's response to an induced magnetic or electromagnetic field may be sampled by a monitoring subsystem. The fluid detection network's response may be sampled without directly contacting the fluid detection network, or at least without establishing a direct charge path between the monitoring subsystem and the fluid detection network. Therefore, this type of sampling is referred to as "wireless." The wirelessly sampled information may be used to assess fluid distribution of a tested area serviced by a fluid detection network.

Monitoring subsystem 300 may include an inducer module 306 configured to wirelessly interact with a fluid detection network. Inducer module 306 may be configured to generate a desired energy field. As a nonlimiting example, inducer module 306 may include a signal generator, such as a radio frequency oscillator, operatively coupled to a coil. The signal generator may drive an electrical signal in either transient or continuous form through the coil to produce a desired energy field. The signal generator may include a voltage-controlled oscillator, phase-lock-loop based synthesizer, direct digital synthesizer, etc. The signal generator may be configured to selectively adjust the waveform, frequency, or duty cycle of the driven signal to produce the desired energy field.

As mentioned above, a monitoring subsystem may be configured to assess a fluid distribution of an area serviced by a fluid detection network, without establishing a physical connection between the fluid detection network and the monitoring subsystem. In such cases, a fluid detection network may be configured to absorb and/or reflect emitted energy in a distinctly different manner according to the fluid distribution of the tested area. The monitoring subsystem may emit an energy field and measure the energy distribution between the monitoring subsystem and the fluid detection network to determine the fluid distribution. For example, at least one characteristic of a network, such as capacitance, impedance, or resonance frequency, may affect a pattern of absorbed energy by the network and/or back-scattered energy reflected from the network. Such characteristic may be indicative of a fluid distribution. Therefore, the characteristic may be determined to assess the fluid distribution.

An energy distribution function may be constructed from two or more measurements. For example, changes in an induced energy field may be periodically measured as the frequency of an induced field is changed. Such measurements may be taken at an analyzing module, a sampling module, or another component of the monitoring subsystem. Thousands or more of such measurements may be taken every second. The results of the measurements may be compiled to form an energy distribution function, which may be graphically represented as a curve. The energy distribution function may be analyzed to determine the state of the corresponding fluid detection network. For example, one or more parameters of the energy distribution function may be compared to a set of stored parameters corresponding to known fluid detection network states. An analyzing module may be used to construct and/or analyze the energy distribution function.

Analysis of an energy distribution function, as opposed to a single measurement, may facilitate identifying the state of a fluid detection network. An energy distribution function, which may include measurements taken at several frequencies over a short period of time, may also be used to compensate for variables that make single measurements less accurate. The pattern of energy exchange may be influenced by variables other than the capacitance of the fluid detection network. For example, a magnetic coupling coefficient K may change according to the proximity and orientation of an inducer and a fluid detection network affecting energy distribution. Analysis of an energy distribution function may be used to identify characteristics of a fluid detection network, such as capacitance, even if the K value changes. Analysis of an energy distribution function may additionally or alternatively compensate for other variables.

As is schematically shown in FIG. 19, monitoring subsystem 300 may include a notification module 310. Notification module 310 may be configured to provide audio, visual, and/or mechanical information that corresponds to the fluid distribution of an area serviced by a fluid detection network. For example, if a tested area is wetted, notification module 310 may turn on a light that indicates the wetted state of the tested area. In some embodiments, the notification module may sound an audible alert, mechanically vibrate, or otherwise generate an indication of a fluid distribution. In some embodiments, the notification module may be configured to provide information corresponding to the individual detectors of a fluid detection network. An amount of information and the resolution of the information presented by a notification module may be selected according to a desired use and the capabilities of the fluid detection network. When present, a notification module may be physically connected to other components of the monitoring subsystem, or the notification module may be a stand-alone unit.

As mentioned above, a fluid detection network may be configured for wireless interaction with a monitoring subsystem. In particular, when exposed to an induced energy field, an energy distribution pattern between a monitoring subsystem and a fluid detection network may be indicative of the fluid distribution of the area serviced by the fluid detection network. Due to the dynamic nature of such a fluid detection network, changes that are caused by the presence of fluid, such as a change in an inductance to capacitance ratio, may cause variations in characteristics of a network, such as impedance, the measure of the voltage and current step-up at resonant frequency, or others. In addition, background noise, changes in temperature, and/or changes in the shape, position, and/or orientation of a fluid detection network may introduce additional test variables. A sampling module 308 may be configured to facilitate data analysis that may be used to reduce dependency on computation of K and/or other test variables. The use of a sampling module may also allow the manufacturing tolerances of the fluid detection network to be more relaxed, resulting in a less expensive testing system.

A sampling module 308 may be positioned within the energy field generated by inducer module 306. The sampling module may include a coil, amplifying circuitry, and/or other componentry configured to measure the induced energy field. The induced energy field may be influenced by external factors, such as a fluid detection network that is at least partially absorbing and/or reflecting energy from the induced energy field. During testing, a sampling module may be positioned within an operating distance of an energy-converting module of a fluid detection network. The sampling module and the energy-converting module may affect each other's response to the induced field. Furthermore, a change in the fluid distribution of the area serviced by the fluid detection network may cause a corresponding change in the energy distribution pattern between the inducer, the fluid detection network, and the sampling module. Such changes in the energy distribution pattern may be used to assess the fluid distribution of an area serviced by the fluid detection network.

Figure 21:
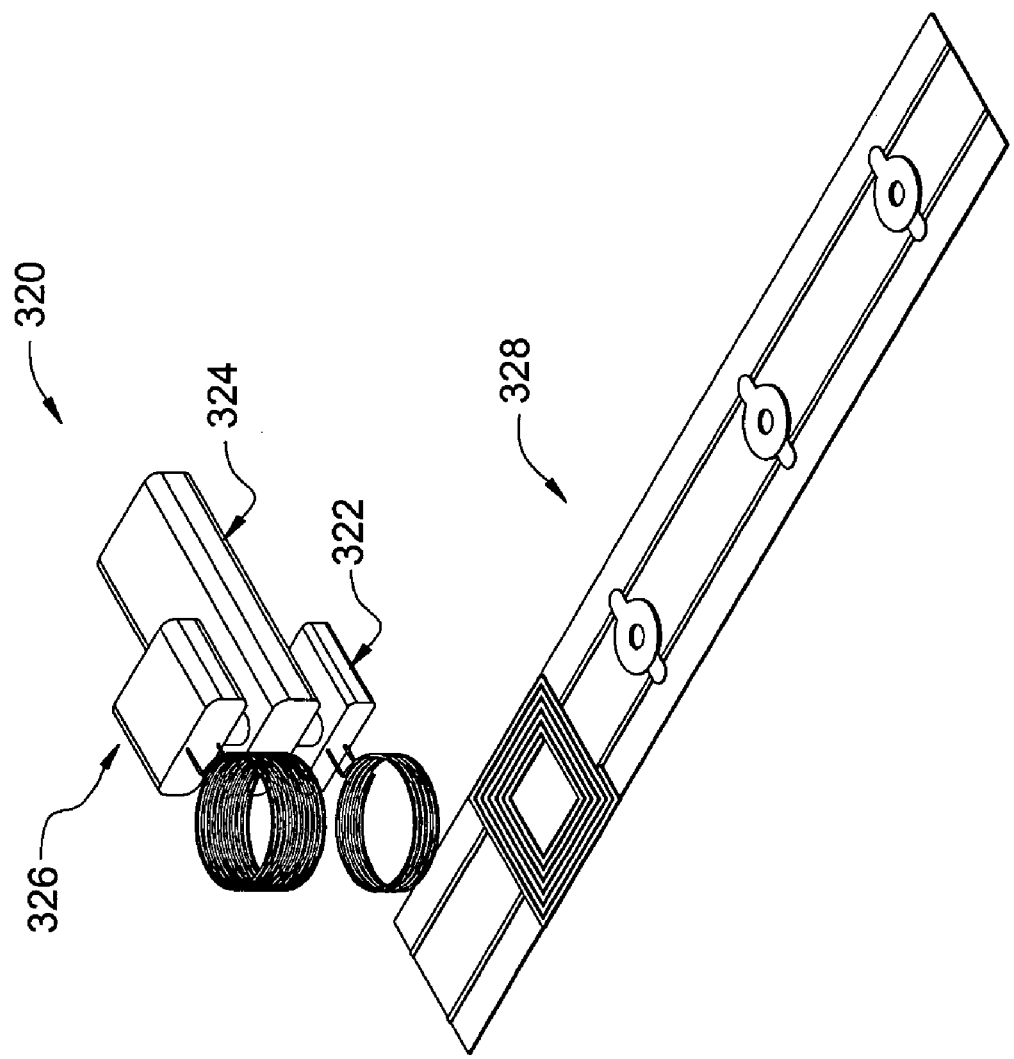
FIG. 21 is a somewhat schematic view of an embodiment of a monitoring subsystem.

As indicated in FIG. 21, a monitoring subsystem 320 may include a sampling module 322 that is physically connected to an analyzing module 324 and an inducer module 326. In this manner, the relative orientation and position of the inducer module and the sampling module are fixed. Therefore, the sampling module and the inducer module move together and may be positioned within an operating distance of a fluid detection network 328 when testing the network. A monitoring subsystem may be configured so that the sampling module is positioned in a certain orientation during testing, such as between the inducer module and the fluid detection network. Such a relationship may allow the sampling module to at least partially mirror changes in the corresponding fluid detection network, provide a fixed reference for computation of variables, and/or reduce dependency on accurate computation of K, as is described in more detail below.

Figure 22:
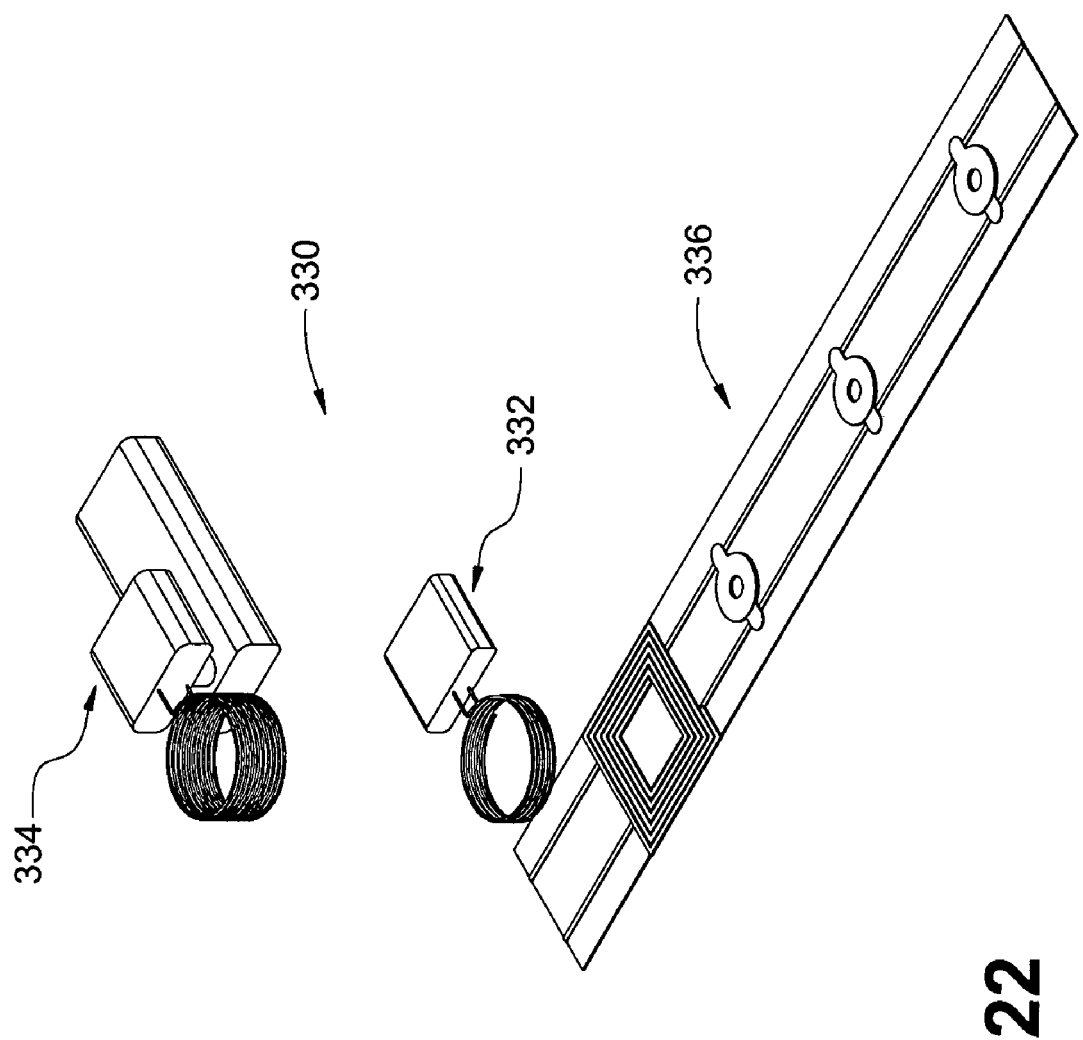
FIG. 22 is a somewhat schematic view of another embodiment of a monitoring subsystem.

As indicated in FIG. 22, a monitoring subsystem 330 may include a sampling module 332 that is a physically independent unit, which is not physically fixed to an inducer module 334. In some embodiments, such a sampling module may be positioned in a substantially fixed relationship relative to a fluid detection network 336. The sampling module may be positioned immediately proximate the fluid detection network, or the sampling module may be separated from the fluid detection network, such as by one or more layers of clothing. For example, the sampling module may be configured for placement in a user's pocket or for direct attachment to an absorbent article.

The network's energy absorption may be influenced by the presence of fluid and therefore the combined energy absorbent pattern of the sampling module and the network's energy-converting module may be indicative of a network's state. The advantage of such a configuration is that while the network's circuitry is kept at a minimum, the sampling module may include componentry that modifies the energy exchange pattern to include information that yields computation of K or other test variables unnecessary. In addition, the sampling module and the monitoring subsystem may be configured so that their relative position at the time of testing may be identified without affecting a network's response. A sampling module may be at least partially self-powered.

Figure 23:
FIGS. 23–26 schematically show a possible analysis used to assess a fluid distribution from a measured energy distribution.

FIG. 23 shows a reference curve 400 (energy distribution function) that represents an energy distribution at a monitoring subsystem. Such a monitoring subsystem may include an inducer configured to generate a signal with known parameters, such as frequency, amplitude, modulation, etc. In particular, the inducer can generate a signal that steps through a range of frequencies, as indicated by the frequency steps comprising the horizontal axis of the illustrated plot. The monitoring subsystem may also include a sampling module at which one or more characteristics of the generated signal may be measured. The measured characteristic may be represented as a quantitative level, as indicated by the vertical axis of the illustrated plot.

The sampling module and the inducer may be positioned in a fixed relationship relative to one another. Fixing the relative position of the sampling module and the inducer may help reduce the number of variables that influence energy exchange between the elements. As an example, a fixed relationship may establish a substantially constant K value between the inducer and the sampling module. Although described with reference to a monitoring subsystem that includes an inducer configured to exchange energy with a sampling module, it should be understood that the disclosed analysis may be used with other arrangements that effectuate a measurable exchange of energy with a fluid detection network.

Reference curve 400 is indicative of a series of measurements taken at the sampling module in a controlled environment, in which external factors are not influencing energy exchange between the sampling module and the inducer. Such a curve may be used as a baseline to which test curves may be compared. In particular, reference curve 400 may be used as a reference to analyze test curves measured when energy exchange between the sampling module and the inducer is influenced by external factors, such as the presence of a fluid detection network.

A fluid detection network may measurably influence energy exchange between an inducer and a sampling module. As the capacitance of the fluid detection network changes in response to a changing fluid distribution, the fluid detection network may cause a corresponding change in the energy exchange between the inducer and the sampling module. The change may be dependent on the relative orientation of the inducer and the sampling module to the urine detection network. Analysis of an energy distribution function may be used to interpret the measured change in the capacitance of the fluid detection network. Such analysis may be made even if the position of the inducer and the sampling module relative to the urine detection network changes within an acceptable range. In other words, changes in the K value can be compensated for by the disclosed analysis. For example, the angle of a test curve relative to a reference curve at the point where the curves intersect may indicate the K value. If the K value is within an acceptable range, the results from the analysis may be reported. If the K value falls out of an acceptable range, additional measurements may be taken and/or a user may be notified to adjust the position of a monitoring subsystem.

Figure 24:
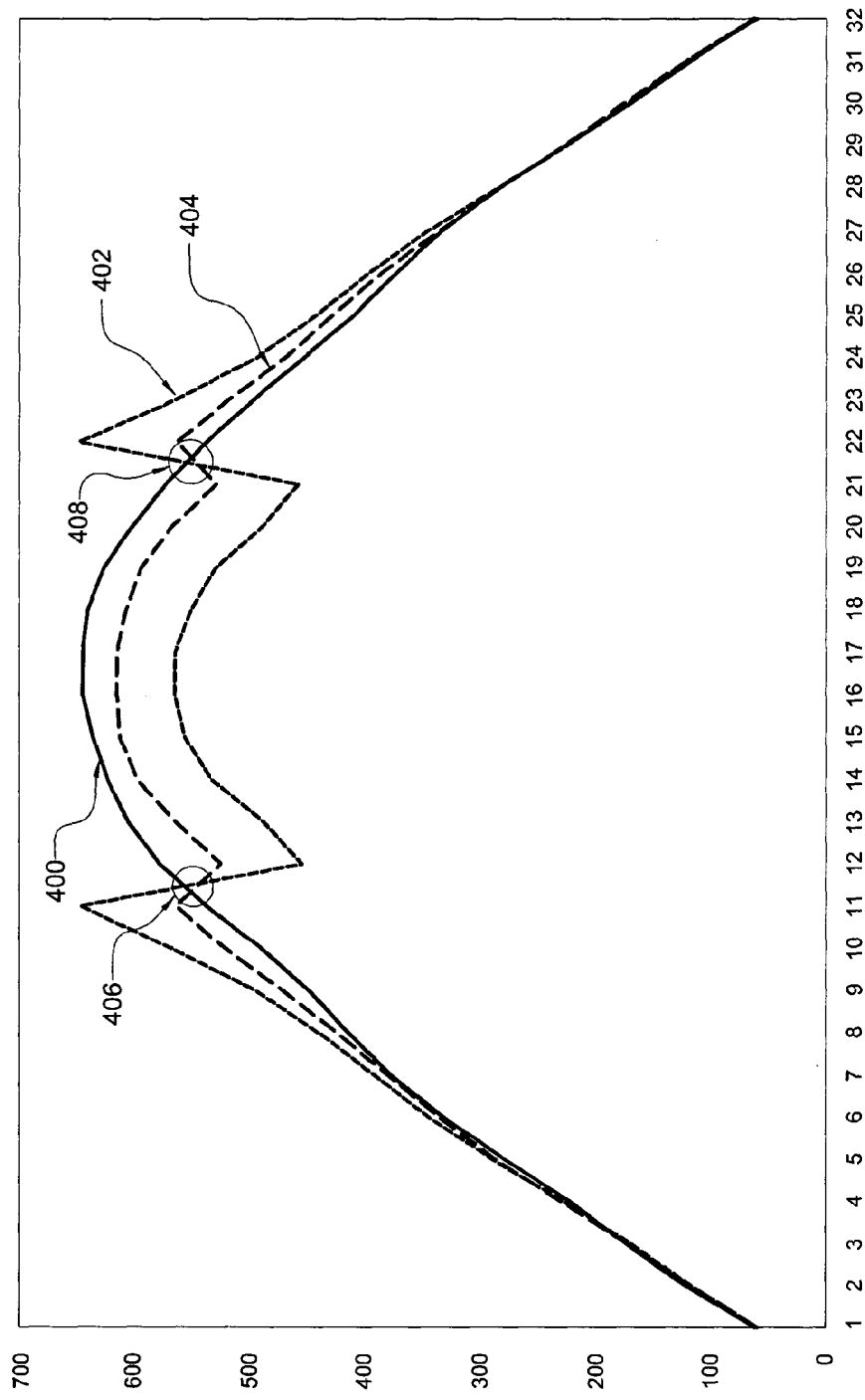

FIG. 24 shows reference curve 400, as well as test curve 402 and test curve 404. Test curve 402 and test curve 404 correspond to a testing situation in which a fluid detection network is queried by a monitoring subsystem positioned so that the sampling module is placed between the inducer and the energy-converting module of a fluid detection network. The test results are influenced by a fluid detection network in a dry state, and thus, each test curve is different from reference curve 400. In other words, the fluid detection network has a capacitance that reflects its dry condition, and the capacitance can be detected by a corresponding change in the energy exchange relative to a situation in which the urine detection network does not influence the energy exchange.

Test curve 402 and test curve 404 correspond to measurements taken when the monitoring subsystem is in two different orientations relative to the fluid detection network. Such differences in orientation are reflected in the differences between the test curves relative to one another. However, despite the differences in the test curves, analysis of the curves can provide information corresponding to the state of the tested fluid detection network.

As can be seen in FIG. 24, test curve 402 and test curve 404 intersect each other at an intersection point 406 and an intersection point 408. Reference curve 400 also passes through intersection point 406 and intersection point 408, or at least within an acceptable range of those points. In other words, both test curves and the reference curve have common intersection points corresponding to a frequency or range of frequencies of the signal generated by the inducer. In the illustrated plot, a dry urine detection network corresponds to intersection points occurring approximately around a frequency step of 11 and a frequency step of 21. Such frequency steps correspond to frequency values, which may be tuned to provide a meaningful reference curve in which energy exchange can be measured. Such results for a dry fluid detection network may be predetermined under known conditions and used as a comparison when testing urine detection networks. For example, a query that yields an intersection point of a test curve compared to a reference curve, or a different test curve, within an acceptable range of predetermined intersection point 406 and/or intersection point 408 may be interpreted as resulting from a urine detection network in a dry condition. This may be true for a range of K values that may be determined by analyzing a test curve, such as by comparing the angle of the test curve relative to the reference curve at the intersection point.

Figure 25:
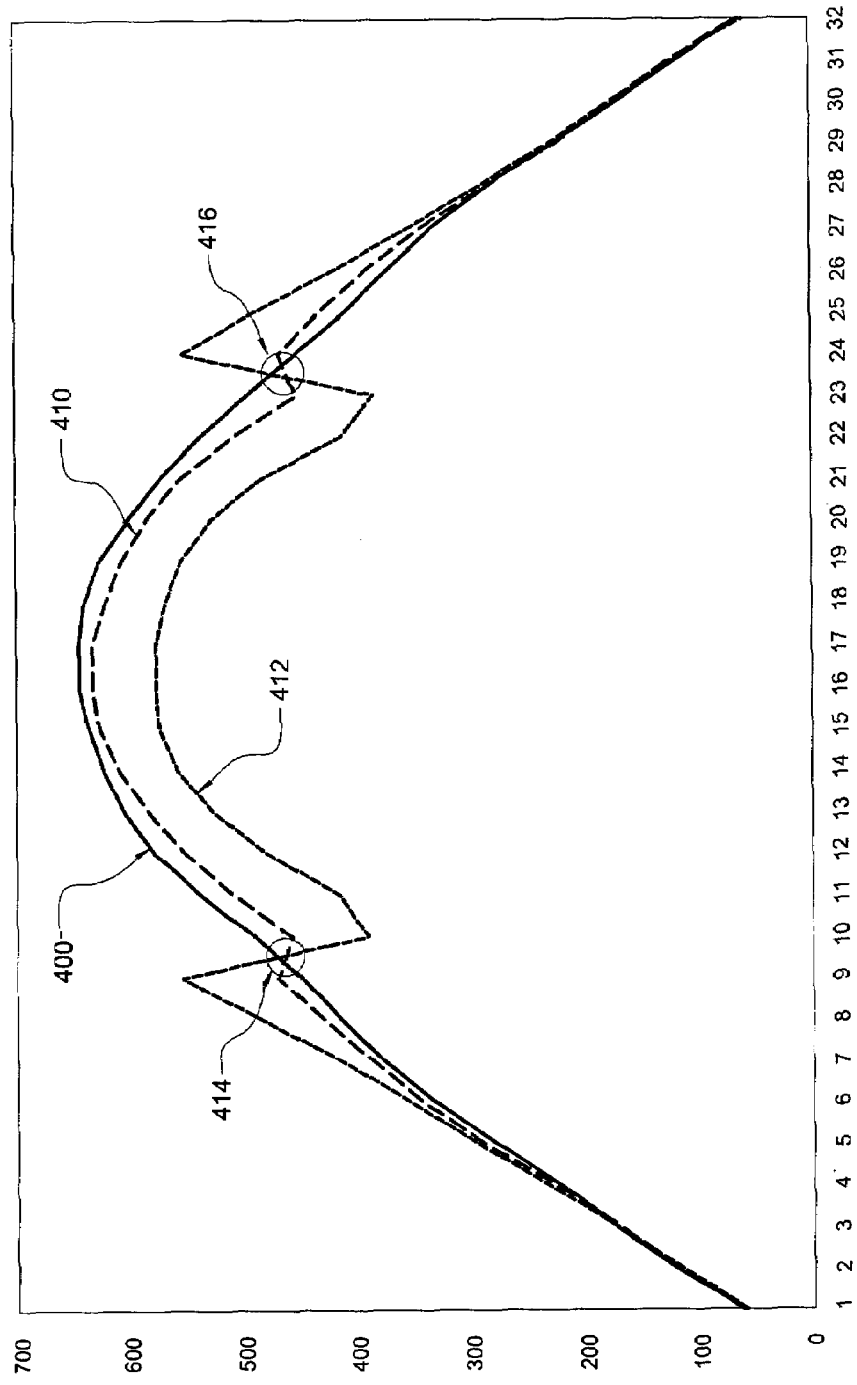

FIG. 25 shows test curve 410 and test curve 412 with reference curve 400. Similar to FIG. 24, the test curves and the reference curves intersect at a common point, or region, as shown at 414 and 416. Intersection points 414 and 416 correspond to a urine detection network in which a first detector is positively testing for urine, and thus is changing the net capacitance of the fluid detection network. The change in capacitance is reflected in the shift of intersection points 414 and 416 when compared to intersection points 406 and 408. The location of the intersection points may be interpreted as resulting from a urine detection network in which the first detector is signaling a fluid distribution in which a region serviced by the first detector is wet.

Figure 26:
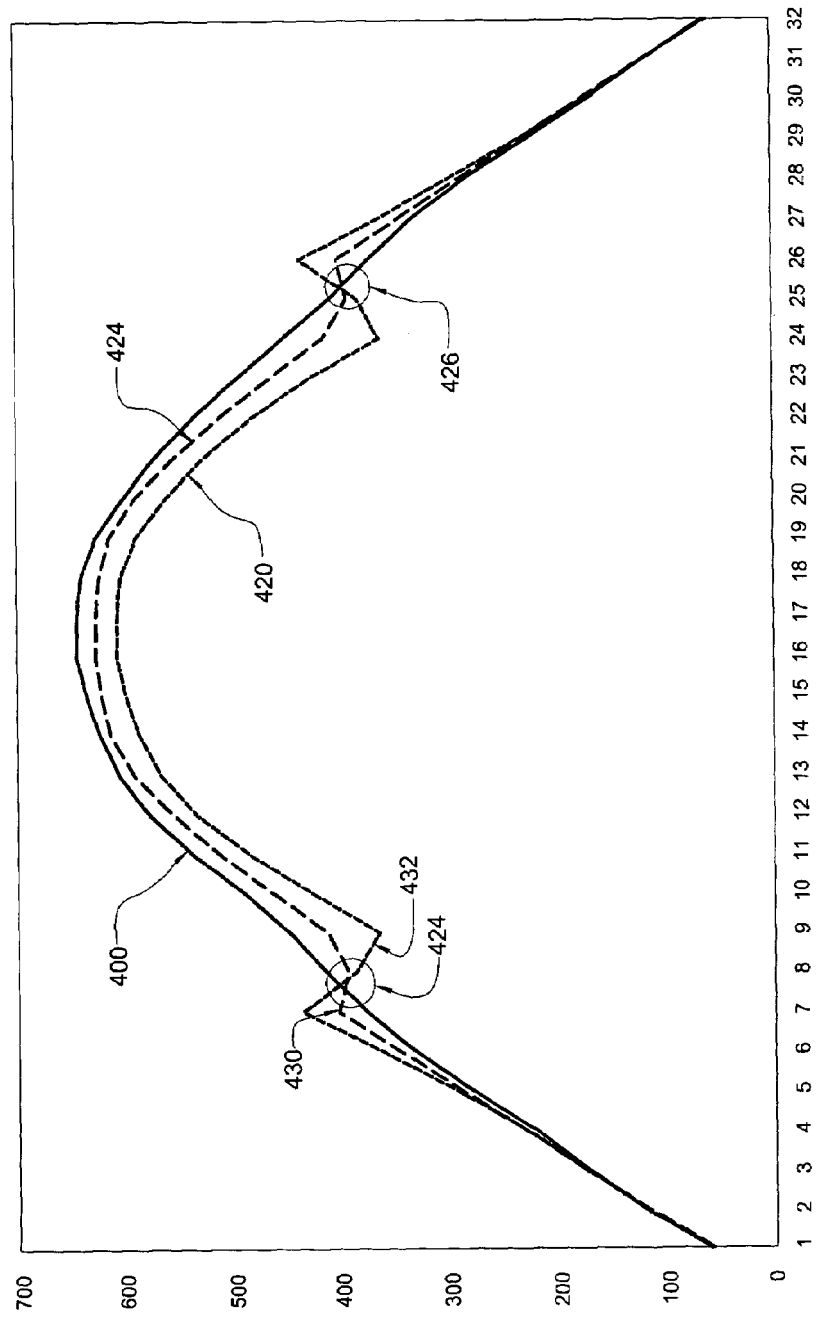

FIG. 26 shows another scenario in which a urine detection network is signaling a wet condition different from that shown in FIG. 25. In other words, a second detector is signaling a wet condition. Therefore, the net capacitance of the urine detection network is different, which is reflected by test curves 420 and 422. As shown, intersection points 424 and 426 are shifted from intersection points 414 and 416 of FIG. 25 and intersection points 406 and 408 of FIG. 24. The location of intersection points 424 and 426 may be interpreted as resulting from a urine detection network in which the second detector is signaling a fluid distribution in which a region serviced by the second detector is wet.

Test curves may be compared to reference curves or to other test curves to identify intersection points, or other relationships that may be used to assess fluid distribution. As explained above, the intersection points are at least partially resistant to variations in K. Therefore, intersection points may be used to identify capacitance values of a urine detection network. Each possible network state may be predetermined under controlled conditions so that such comparisons may be made (first detector wet, second detector wet, first and second detector wet, etc.) As mentioned above, the network may be configured so that each possible network state has a unique net capacitance. As can be appreciated, changes in the capacitance of a urine detection network cause a corresponding measurable change in energy distribution. Such changes may be analyzed by comparing tested responses with known responses that have been predetermined. In this manner, analysis may be used to determine the state of a urine detection network. Because the analysis can be performed with differing K values, which correspond to different monitoring subsystem positions and/or orientations, flexibility in testing scenarios is achieved.

In some embodiments, aspects of a test curve, and/or reference curve, other than an intersection point may be analyzed. For example, test curves typically experience a deviation, such as deviation 430 and deviation 432 of FIG. 27. Such deviations may be analyzed to determine the capacitance of a measured urine detection network. Analysis may include position of inflection points bounding a deviation, distance between inflection points bounding a deviation, and/or angle of deviation. Other criteria for analyzing test curves are contemplated. In particular, other comparisons between test curves and a reference curve may be used to interpret the capacitance of a urine detection network.

Furthermore, two or more energy distribution functions, such as energy distribution functions constructed from sets of measurements taken at different times, may be compared to one another. Comparisons between two or more energy distribution functions may be used to assess information about the state of a fluid detection network and/or to verify test results.

Background noise, or interference, may affect the results of one or more test measurements. To accurately detect the state of a network, the effects of interference on a test curve may need to be identified and compensated for. The use of a sampling module that yields a reference curve may provide the ability to detect interference. For example, a test curve that is substantially different from the reference curve, while the sampling module is positioned away from the influence of a network, may provide an indication of interference. Analyzing such test curves may provide information about the interference pattern and may be used to exclude the effects of interference from further measurements. In addition, numerical and statistical filters may be applied to detect adverse effects of a transient interference and/or a fluctuating interference. As used herein, background noise and interference includes anything besides a tested fluid detection network that is affecting measurements taken by a monitoring subsystem. In other words, any signal, information, energy field, etc. received outside of an information link established between a monitoring subsystem and a fluid detection network may be referred to as background noise and/or interference.

In some embodiments, more than one sampling module may be used in taking differential measurements that may overcome the adverse effects of background noise on measurements. For example, two sampling modules may be fixed on opposite sides of an inducer module at substantially equal distances from the inducer module. Measurements of induced signals at both locations will result in two test curves. When no network is present, the test curves should be substantially similar, even in a noisy environment, as both will respond similarly to the noise. When a network is present, both modules will respond according to the respective distance and orientation of the sampling module relative to the network and the inducer. The difference between the two test curves may be attributed to the position of the sampling modules relative to the fluid detection network and/or the state of the fluid detection network.

Although the present disclosure has been provided with reference to the foregoing operational principles and embodiments, it will be apparent to those skilled in the art that various changes in form and detail may be made without departing from the spirit and scope defined in the appended claims. The present disclosure is intended to embrace all such alternatives, modifications and variances. Where the disclosure or claims recite "a," "a first," or "another" element, or the equivalent thereof, they should be interpreted to include one or more such elements, neither requiring nor excluding two or more such elements.

What is claimed is:

1. A monitoring subsystem for assessing an energy-absorption pattern of an energy-converting module, the monitoring subsystem comprising:
   an inducer module configured to establish an energy distribution between the energy-converting module and the monitoring subsystem;
   a sampling module configured to measure the energy distribution; and
   an analyzing module configured to determine the energy-absorption pattern of the energy-converting module by comparing the measured energy distribution to a reference energy distribution, wherein the reference energy distribution corresponds to an energy distribution unaffected by the energy-converting module and measured at the sampling module.

2. The monitoring subsystem of claim 1, wherein the analyzing module includes a memory, and wherein the reference energy distribution is stored in the memory.

3. The monitoring subsystem of claim 1, wherein the analyzing module is configured to recognize interference by comparing the measured energy distribution to the reference energy distribution.

4. The monitoring subsystem of claim 3, wherein the analyzing module is configured to compensate for the interference.

5. The monitoring subsystem of claim 3, further comprising a notification module, wherein the notification module is configured to report that an environment is not suitable for detection if the interference cannot be compensated for.

6. The monitoring subsystem of claim 3, further comprising a notification module, wherein the notification module is configured to report that an environment is suitable for detection if an uncorrectable interference is not present.

7. The monitoring subsystem of claim 1, wherein the sampling module is positionally fixed relative to the inducer module.

8. The monitoring subsystem of claim 1, wherein the analyzing module is configured to find an intersection of the measured energy distribution and the reference energy distribution.

9. The monitoring subsystem of claim 8, wherein the analyzing module uses a frequency of the intersection to look up the energy-absorption pattern.

10. The monitoring subsystem of claim 8, wherein the analyzing module uses an angle of the intersection to look up the energy-absorption pattern.

11. The monitoring subsystem of claim 1, wherein the analyzing module is configured to determine the energy-absorption pattern of the energy-converting module by comparing the reference energy distribution and two or more measured energy distributions from different times.

12. The monitoring subsystem of claim 11, wherein the two measured energy distributions correspond to two different positions of the inducer module relative to the energy-converting module.

13. The monitoring subsystem of claim 11, wherein the two measured energy distributions are measured by different sampling modules.

14. The monitoring subsystem of claim 1, further comprising a notification module configured to report the energy-absorption pattern.

15. The monitoring subsystem of claim 1, wherein the energy converting module is an LC circuit.

16. The monitoring subsystem of claim 1, wherein the monitoring subsystem is configured for assessing a fluid distribution of a test area serviced by a urine detection network, wherein the urine detection network has a net characteristic indicative of the fluid distribution of the test area, wherein the inducer module is configured to generate an energy field, wherein an energy field is generated within an operative distance of the urine detection network to establish an energy distribution between the urine detection network and the monitoring subsystem that is predictably influenced by the net characteristic of the urine detection network, and wherein the analyzing module is configured to determine the net characteristic of the urine detection network from the energy distribution between the urine detection network and the monitoring subsystem.

17. The monitoring subsystem of claim 16, wherein the analyzing module is configured to determine the net characteristic of the urine detection network by comparing two or more measured energy distributions measured at different times.

18. The monitoring subsystem of claim 16, further comprising a notification module configured to report a fluid distribution derived from the determined net characteristic.

19. The monitoring subsystem of claim 16, wherein the net characteristic is capacitance.

20. A monitoring subsystem for assessing an energy-absorption pattern of an energy-converting module, the monitoring subsystem comprising:
    an inducer module configured to establish an energy distribution between the energy-converting module and the monitoring subsystem;
    a sampling module configured to measure the energy distribution; and
    an analyzing module configured to determine the energy-absorption pattern of the energy-converting module by comparing the measured energy distribution to a reference energy distribution,
    wherein the monitoring subsystem is configured for assessing a fluid distribution of a test area serviced by a urine detection network, wherein the urine detection network has a net characteristic indicative of the fluid distribution of the test area, wherein the inducer module is configured to generate an energy field, wherein an energy field is generated within an operative distance of the urine detection network to establish an energy distribution between the urine detection network and the monitoring subsystem that is predictably influenced by the net characteristic of the urine detection network, wherein the analyzing module is configured to determine the net characteristic of the urine detection network from the energy distribution between the urine detection network and the monitoring subsystem, and wherein the analyzing module is configured to recognize interference by comparing the measured energy distribution to the reference energy distribution.

21. The monitoring subsystem of claim 20, wherein the analyzing module is configured to compensate for the interference.

22. The monitoring subsystem of claim 20, further comprising a notification module, wherein the notification module is configured to report that an environment is not suitable for detection if the interference cannot be compensated for.

23. The monitoring subsystem of claim 20, further comprising a notification module, wherein the notification module is configured to report that an environment is suitable for detection if an uncorrectable interference is not present.

24. A monitoring subsystem for assessing an energy-absorption pattern of an energy-converting module, the monitoring subsystem comprising:
    an inducer module configured to establish an energy distribution between the energy-converting module and the monitoring subsystem;
    a sampling module configured to measure the energy distribution; and
    an analyzing module configured to determine the energy-absorption pattern of the energy-converting module by comparing the measured energy distribution to a reference energy distribution,
    wherein the analyzing module is configured to determine the energy-absorption pattern of the energy-converting module by comparing the reference energy distribution and two or more measured energy distributions from different times.

25. The monitoring subsystem of claim 24, wherein the analyzing module is configured to determine the energy-absorption pattern of the energy-converting module by finding an intersection point of the two measured energy distributions.

26. The monitoring subsystem of claim 25, wherein the two measured energy distributions correspond to two different positions of the inducer module relative to the energy-converting module.

27. The monitoring subsystem of claim 24, wherein the two measured energy distributions are measured by different sampling modules.

* * * * *